(12) United States Patent
Paul et al.

(10) Patent No.: US 8,167,948 B2
(45) Date of Patent: May 1, 2012

(54) ANTERIOR PROSTHETIC SPINAL DISC REPLACEMENT

(75) Inventors: David C. Paul, Phoenixville, PA (US); Christopher Angelucci, Schwenksville, PA (US); William Rhoda, Drexel Hill, PA (US); Michael L. Boyer, II, Paoli, PA (US); William E. Duffield, Collegeville, PA (US)

(73) Assignee: Globus Medical, Inc., Audubon, PA (US)

( * ) Notice: Subject to any disclaimer, the term of this patent is extended or adjusted under 35 U.S.C. 154(b) by 1295 days.

(21) Appl. No.: 11/246,149

(22) Filed: Oct. 11, 2005

(65) Prior Publication Data
US 2006/0036325 A1 Feb. 16, 2006

(51) Int. Cl.
*A61F 2/44* (2006.01)
(52) U.S. Cl. ................................. 623/17.16
(58) Field of Classification Search ..... 623/17.11–17.16
See application file for complete search history.

(56) References Cited

U.S. PATENT DOCUMENTS

| | | | |
|---|---|---|---|
| 4,550,450 A * | 11/1985 | Kinnett | 623/20.11 |
| 4,759,766 A | 7/1988 | Buettner-Janz et al. | |
| 4,997,432 A | 3/1991 | Keller | |
| 5,122,130 A | 6/1992 | Keller | |
| 5,246,458 A | 9/1993 | Graham | |
| 5,258,031 A | 11/1993 | Salib et al. | |
| 5,314,477 A | 5/1994 | Marnay | |
| 5,401,269 A | 3/1995 | Buttner-Janz et al. | |
| 5,425,773 A | 6/1995 | Boyd et al. | |
| 5,507,816 A | 4/1996 | Bullivant | |
| 5,534,029 A | 7/1996 | Shima | |
| 5,556,431 A | 9/1996 | Buttner-Janz | |
| 5,562,738 A | 10/1996 | Boyd et al. | |
| 5,676,701 A | 10/1997 | Yuan et al. | |
| 5,683,465 A | 11/1997 | Shinn et al. | |
| 5,755,796 A | 5/1998 | Ibo | |
| 5,888,226 A | 3/1999 | Rogozinski | |
| 5,895,428 A | 4/1999 | Berry | |
| 5,899,941 A | 5/1999 | Nishijima et al. | |
| 6,039,763 A | 3/2000 | Shelokov | |
| 6,063,121 A | 5/2000 | Xavier et al. | |
| 6,080,157 A | 6/2000 | Cathro et al. | |
| 6,113,637 A | 9/2000 | Gill et al. | |
| 6,146,421 A | 11/2000 | Gordon | |
| 6,146,422 A | 11/2000 | Lawson | |
| 6,156,067 A | 12/2000 | Bryan et al. | |
| 6,228,118 B1 | 5/2001 | Gordon | |
| 6,368,350 B1 | 4/2002 | Erickson et al. | |
| 6,375,682 B1 | 4/2002 | Fleischmann et al. | |

(Continued)

FOREIGN PATENT DOCUMENTS
EP 0955021 3/1998
(Continued)

OTHER PUBLICATIONS

U.S. Appl. No. 10/909,210, David Paul et al.
(Continued)

*Primary Examiner* — Nicholas Woodall

(57) ABSTRACT

The present invention relates generally to a prosthetic spinal disc for replacing a damaged disc between two vertebrae of a spine. The present invention also relates to a method for implanting a prosthetic spinal disc via anterior or anterior lateral implantation. Other surgical approaches for implanting the prosthetic disc may also be used.

9 Claims, 21 Drawing Sheets

U.S. PATENT DOCUMENTS

| | | | |
|---|---|---|---|
| 6,416,551 | B1 | 7/2002 | Keller |
| 6,468,310 | B1 | 10/2002 | Ralph et al. |
| 6,540,785 | B1 | 4/2003 | Gill et al. |
| 6,635,087 | B2 | 10/2003 | Angelucci et al. |
| 6,660,007 | B2 | 12/2003 | Khanna |
| 6,682,562 | B2 | 1/2004 | Viart et al. |
| 6,706,068 | B2 | 3/2004 | Ferree |
| 6,712,852 | B1 | 3/2004 | Chung et al. |
| 6,966,929 | B2 * | 11/2005 | Mitchell ............... 623/17.11 |
| 6,997,953 | B2 | 2/2006 | Chung et al. |
| 7,637,955 | B2 * | 12/2009 | Marik et al. ............ 623/17.14 |
| 7,641,666 | B2 | 1/2010 | Paul et al. |
| 2002/0035400 | A1 | 3/2002 | Bryan et al. |
| 2002/0111681 | A1 | 8/2002 | Ralph et al. |
| 2002/0111682 | A1 | 8/2002 | Ralph et al. |
| 2002/0111683 | A1 | 8/2002 | Ralph et al. |
| 2002/0111684 | A1 | 8/2002 | Ralph et al. |
| 2002/0111685 | A1 | 8/2002 | Ralph et al. |
| 2002/0111686 | A1 | 8/2002 | Ralph et al. |
| 2002/0111687 | A1 | 8/2002 | Ralph et al. |
| 2002/0120335 | A1 | 8/2002 | Angelucci et al. |
| 2003/0045935 | A1 | 3/2003 | Angelucci et al. |
| 2003/0045936 | A1 | 3/2003 | Angelucci et al. |
| 2003/0125738 | A1 | 7/2003 | Khanna |
| 2003/0125740 | A1 | 7/2003 | Khanna |
| 2003/0204261 | A1 | 10/2003 | Eisermann et al. |
| 2003/0233094 | A1 | 12/2003 | Squires |
| 2004/0030388 | A1 | 2/2004 | Null et al. |
| 2004/0064184 | A1 | 4/2004 | Chung et al. |
| 2004/0111160 | A1 * | 6/2004 | Evans et al. ............. 623/17.14 |
| 2004/0117022 | A1 | 6/2004 | Marnay et al. |
| 2004/0138750 | A1 | 7/2004 | Mitchell |
| 2004/0143332 | A1 | 7/2004 | Krueger |
| 2004/0153155 | A1 | 8/2004 | Chung et al. |
| 2004/0153157 | A1 | 8/2004 | Keller |
| 2004/0172135 | A1 | 9/2004 | Mitchell |
| 2004/0210222 | A1 | 10/2004 | Angelucci et al. |
| 2004/0215198 | A1 | 10/2004 | Marnay |
| 2004/0220582 | A1 | 11/2004 | Keller |
| 2004/0225365 | A1 | 11/2004 | Eisermann et al. |
| 2004/0243240 | A1 | 12/2004 | Beaurain |
| 2005/0021145 | A1 | 1/2005 | de Villiers et al. |
| 2005/0038511 | A1 | 2/2005 | Martz |
| 2005/0043800 | A1 | 2/2005 | Paul et al. |
| 2005/0107877 | A1 | 5/2005 | Blain |
| 2005/0131412 | A1 | 6/2005 | Olevsky et al. |
| 2005/0216086 | A1 * | 9/2005 | Marik et al. ............ 623/17.15 |
| 2005/0251138 | A1 | 11/2005 | Boris et al. |
| 2005/0261773 | A1 | 11/2005 | Ferree |
| 2005/0273100 | A1 | 12/2005 | Taylor |
| 2006/0116768 | A1 | 6/2006 | Krueger et al. |
| 2007/0010826 | A1 | 1/2007 | Rhoda et al. |
| 2007/0055378 | A1 | 3/2007 | Ankney et al. |
| 2007/0260317 | A1 | 11/2007 | Paul et al. |

FOREIGN PATENT DOCUMENTS

| | | |
|---|---|---|
| WO | WO 99/05995 | 2/1999 |
| WO | WO 00/23015 | 4/2000 |
| WO | WO 00/42944 | 7/2000 |
| WO | PCT/US2004/024933 | 10/2006 |
| WO | PCT/US2004/024933 | 12/2006 |

OTHER PUBLICATIONS

U.S. Appl. No. 11/318,438, David Paul et al.

U.S. Appl. No. 11/364,160, William Rhoda et al.

U.S. Appl. No. 11/366,390, David Ankney et al.

* cited by examiner

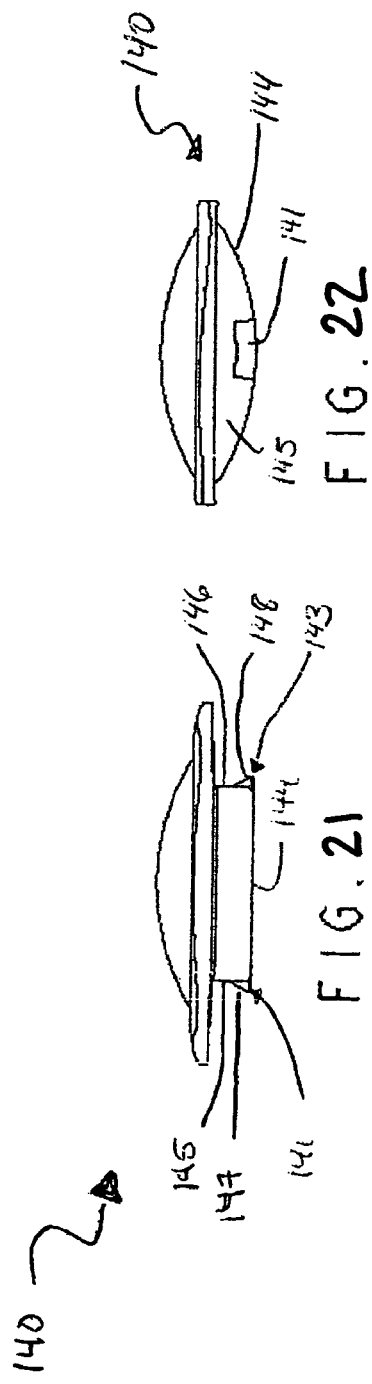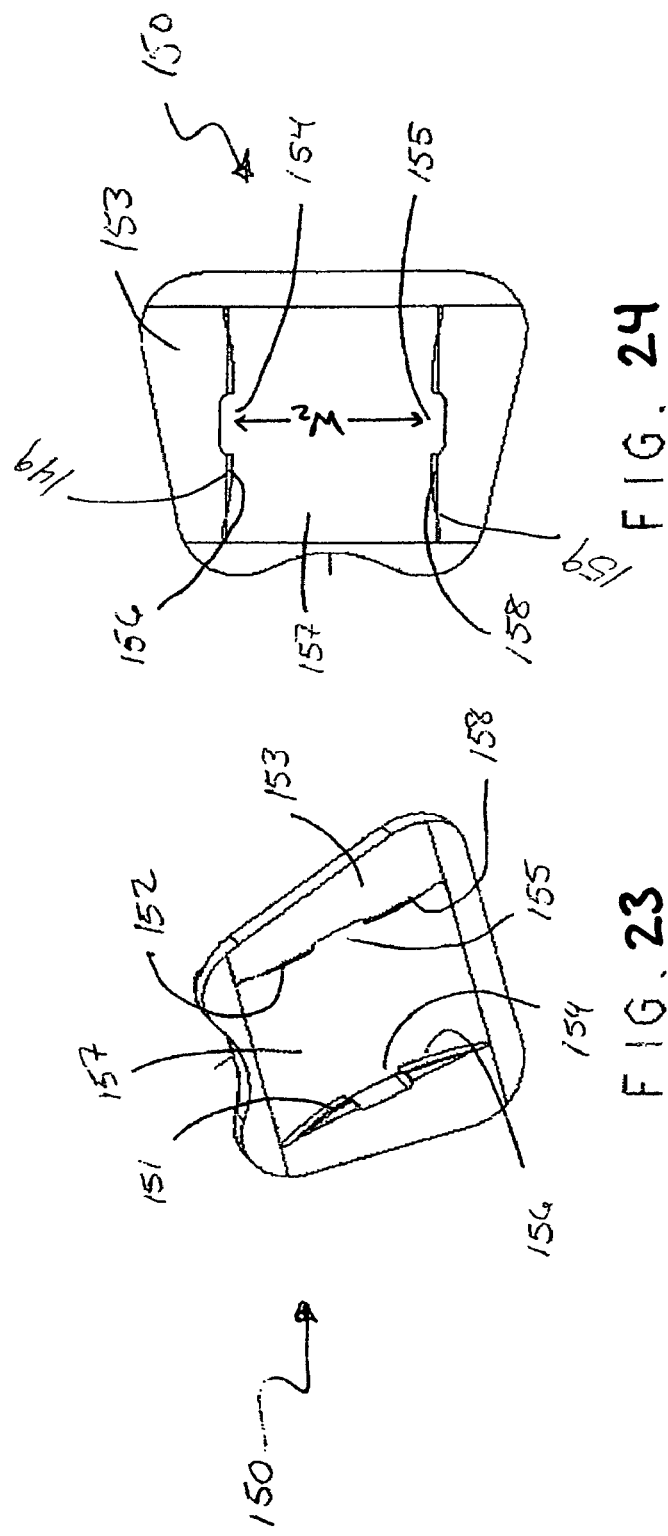

ANTERIOR PROSTHETIC SPINAL DISC REPLACEMENT

CROSS REFERENCE TO RELATED APPLICATIONS

This application claims priority to U.S. application Ser. No. 10/909,210 filed on Jul. 30, 2004, now U.S. Pat. No. 7,641,666, U.S. application Ser. No. 10/827,642 filed on Apr. 20, 2004, now U.S. Pat. No. 7,621,956, and to provisional application Ser. No. 60/491,271 filed on Jul. 31, 2003, all of which are incorporated in their entireties by reference thereto.

FIELD OF THE INVENTION

The present invention relates to a prosthetic spinal disc for fully or partially replacing a damaged disc between two vertebrae of a spine. The present invention also relates to a method for implanting a prosthetic spinal disc via anterior, anterolateral, and lateral implantation, although other implantation approaches may also be used.

BACKGROUND OF THE INVENTION

The vertebral spine is the axis of the skeleton on which a substantial portion of the weight of the body is supported. In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints and allow known degrees of flexion, extension, lateral bending, and axial rotation.

The typical vertebra has a thick anterior bone mass called the vertebral body, with a neural (vertebral) arch that arises from the posterior surface of the vertebral body. The centra of adjacent vertebrae are supported by intervertebral discs. Each neural arch combines with the posterior surface of the vertebral body and encloses a vertebral foramen. The vertebral foramina of adjacent vertebrae are aligned to form a vertebral canal, through which the spinal sac, cord and nerve rootlets pass. The portion of the neural arch which extends posteriorly and acts to protect the spinal cord's posterior side is known as the lamina. Projecting from the posterior region of the neural arch is the spinous process.

The intervertebral disc primarily serves as a mechanical cushion permitting controlled motion between vertebral segments of the axial skeleton. The normal disc is a unique, mixed structure, comprised of three component tissues: the nucleus pulpous ("nucleus"), the annulus fibrosus ("annulus") and two vertebral end plates. The two vertebral end plates are composed of thin cartilage overlying a thin layer of hard, cortical bone which attaches to the spongy, richly vascular, cancellous bone of the vertebral body. The end plates thus act to attach adjacent vertebrae to the disc. In other words, a transitional zone is created by the end plates between the malleable disc and the bony vertebrae.

The annulus of the disc is a tough, outer fibrous ring which binds together adjacent vertebrae. The fibrous portion, which is much like a laminated automobile tire, measures about 10 to 15 millimeters in height and about 15 to 20 millimeters in thickness. The fibers of the annulus consist of fifteen to twenty overlapping multiple plies, and are inserted into the superior and inferior vertebral bodies at roughly a 40 degree angle in both directions. This configuration particularly resists torsion, as about half of the angulated fibers will tighten when the vertebrae rotates in either direction, relative to each other. The laminated plies are less firmly attached to each other.

Immersed within the annulus is the nucleus. The healthy nucleus is largely a gel-like substance having high water content, and like air in a tire, serves to keep the annulus tight yet flexible. The nucleus-gel moves slightly within the annulus when force is exerted on the adjacent vertebrae while bending, lifting, and other motions.

The spinal disc may be displaced or damaged due to trauma, disease, degenerative defects, or wear over an extended period. A disc herniation occurs when the annulus fibers are weakened or torn and the inner tissue of the nucleus becomes permanently bulged, distended, or extruded out of its normal, internal annulus confines. The mass of a herniated or "slipped" nucleus tissue can compress a spinal nerve, resulting in leg pain, loss of muscle control, or even paralysis. Alternatively, with discal degeneration, the nucleus loses its water binding ability and deflates, as though the air had been let out of a tire. Subsequently, the height of the nucleus decreases causing the annulus to buckle in areas where the laminated plies are loosely bonded. As these overlapping laminated plies of the annulus begin to buckle and separate, either circumferential or radial annular tears may occur, which may contribute to persistent or disabling back pain. Adjacent, ancillary spinal facet joints will also be forced into an overriding position, which may create additional back pain.

Whenever the nucleus tissue is herniated or removed by surgery, the disc space will narrow and may lose much of its normal stability. In many cases, to alleviate back pain from degenerated or herniated discs, the nucleus is removed and the two adjacent vertebrae are surgically fused together. While this treatment alleviates the pain, all discal motion is lost in the fused segment. Ultimately, this procedure places a greater stress on the discs adjacent to the fused segment as they compensate for lack of motion, perhaps leading to premature degeneration of those adjacent discs.

As an alternative to vertebral fusion, various prosthetic discs have been developed. The first prosthetics embodied a wide variety of ideas, such as ball bearings, springs, metal spikes and other perceived aids. These prosthetics are all made to replace the entire intervertebral disc space and are large and rigid. These devices have met with less than ideal results and improved designs are needed.

While anterior implantation involves numerous risks during surgery, including potential damage to organs during surgery and increased risk to the various blood vessels during surgery, improved designs and methods of implantation may increase the desirability of anterior approaches to prosthetic disc replacements.

A posterior approach to intervertebral disc implantation avoids the risks of damaging body organs and vessels. Despite this advantage, a posterior approach also raises other difficulties that have discouraged it use. For instance, during a posterior approach the spinal cord is exposed and potentially at risk of damage. Additionally, vertebral body geometry allows only limited access to the intervertebral discs. Thus, the key to successful posterior or posterior lateral implantation is avoiding contact with the spinal cord, as well as being able to place an implant through a limited special area due to the shape of the vertebral bones.

Accordingly, there exists a need for improved designs for prosthetic discs. In particular, an improved design for prosthetic discs for anterior implantation are needed. Accordingly, the present invention provides improved designs for prosthetic discs implanted into a patient from the anterior approach.

SUMMARY OF THE INVENTION

Generally, the present invention is directed toward prosthetic disc designs. One embodiment of the invention is a prosthetic disc for replacement of a damaged spinal disc between two vertebrae. The prosthetic disc has endplates made of rigid material. One plate of rigid material has a surface that can engage with a surface of a vertebral body. The rigid plate may have a contoured, partially spherical articulating surface. A second rigid plate having a second surface engages with the surface of a second vertebral body, and has a contoured, partially cylindrical articulating surface. A core element may be at least partially disposed between the first and second rigid plates. Moreover, the core element may have contoured surfaces in communication with and substantially corresponding to the curvature of the first and second rigid plate articulating surfaces.

In one embodiment, one or both of the rigid plates are configured to correspond to the natural curvature and shape of the vertebral body endplates. In another embodiment, however, one or both of the rigid plates are configured to have a preselected shape or contour. Thus, the surface of the vertebral body that contacts the rigid plate may be shaped or prepared for receiving or mating with the preselected shape or contour of the one or more rigid plates. In one example embodiment, the portion of one or both plates that contacts a vertebral body is substantially flat.

In another embodiment, the prosthetic disc is formed from a plurality of assemblies. The first assembly comprises the first rigid plate, second rigid plate, and core element. The second assembly comprises a third rigid plate configured and adapted to engage with the first endplate of the first vertebral body, and has a contoured, partially spherical articulating surface having substantially the same radius of curvature as the first rigid plate articulating surface. The second assembly also may have a fourth rigid plate configured and adapted to engage with the second endplate of the second vertebral body, and having a contoured, partially cylindrical articulating surface having substantially the same radius of curvature as the second rigid plate articulating surface. Likewise, the second assembly may have a second core element at least partially disposed between the third and fourth rigid plates, wherein the second core element has a contoured surfaces substantially corresponding to the curvature of the third and fourth rigid plate articulating surfaces.

Several embodiments of the present invention are directed toward an artificial disc that is capable of providing a moving instantaneous axis of rotation (IAR). In one embodiment, the moving IAR achieved is substantially in the sagittal plane.

In many embodiments, the contact between the first rigid plate articulating surface and the first contoured surface of the first core element extends over an area. Likewise, the second rigid plate articulating surface and the second contoured surface of the first core element may also extend over an area. While it is preferred that both the first and second articulating surfaces contact the core element over an area, one or both surfaces may be configured to contact the core element along a line or a point. For instance, in one embodiment the contact between the second rigid plate articulating surface and the second contoured surface of the first core element forms a line of contact.

In some embodiments, the orientation or relative position of the articulating surfaces may be specified. For example, in one embodiment, the first rigid plate is disposed above the first core element and the second rigid plate is disposed below the first core element.

In another embodiment, one or both rigid plates may have a keel or raised ridge of material that extends at least partially into the endplate of the vertebral body that they contact.

A variety of materials may be used to form the components of the invention. For instance, in one embodiment the first core element is at least partially formed of an elastomeric material.

The artificial disc may also have mechanical stops that limit movement of the disc. For example, stops may be provided to prevent lateral bending greater than 10 degrees in each direction. In addition, mechanical stops may prevent total axial rotation greater than 5 to 10 degrees.

The curvature of the articulating surfaces may be convex or concave. In one embodiment, the curvature of the second rigid plate articulating surface is convex. In another embodiment, the curvature of the second rigid plate articulating surface is concave. The dimensions of each component also may be varied. For example, in one embodiment the first rigid plate may have a length from about 10 to about 45 mm, while in another embodiment the first rigid plate may have a length from about 22 to about 26 mm. In yet another embodiment, the first rigid plate may have a width from about 7 mm to about 36 mm, or alternatively may be from about 7 mm to about 15 mm. In still another embodiment, the first rigid plate has a width from about 8 to about 12 mm, and in a further embodiment the first rigid plate has a width from about 12 mm to about 36 mm. Moreover, other embodiments the first rigid plate may have a width from about 16 mm to about 28 mm, or from about 12 to abut 14 mm.

In one embodiment the core element and endplates are formed from substantially similar materials, while in another embodiment the core element is formed from a different material that the endplates. In one embodiment, the core comprises a high molecular weight polymeric material, and more specifically may comprise a high molecular weight polyethylene. The core may also be formed from polyetherketone (PEEK) or other radio translucent materials. In embodiments where radio translucent materials are used, the core may have a radio opaque marker that is capable of indicating the orientation of the core. For example, the radio opaque marker may be two or more metallic pins with orientations that permit identification of the orientation of the core. Additionally, all components of the prosthetic disc may be made out of metal. Preferably, when metal is used as the material to make the prosthetic disc, a biocompatible metal, such as cobalt-chromium or titanium, is used.

Methods for replacing a damaged spinal disc between two vertebrae and tools and/or instruments thereof are also contemplated by the present invention. One embodiment involves the steps of removing a damaged spinal disc disposed between two vertebral bodies, providing and positioning a first artificial disc assembly therebetween. In some instances, one or both endplates of the vertebral bodies may be prepared for receiving the artificial disc.

BRIEF DESCRIPTION OF THE DRAWINGS

The invention will be more readily understood with reference to the embodiments thereof illustrated in the attached figures, in which:

FIG. 21 is an illustration of a core member of an embodiment of the present invention;

FIG. 23 is an illustration of an endplate of an embodiment of the present invention;

FIG. 24 is an illustration of an endplate of an embodiment of the present invention;

FIG. 27 is an illustration of an endplate of an embodiment of the present invention.

DETAILED DESCRIPTION

Figure 1:
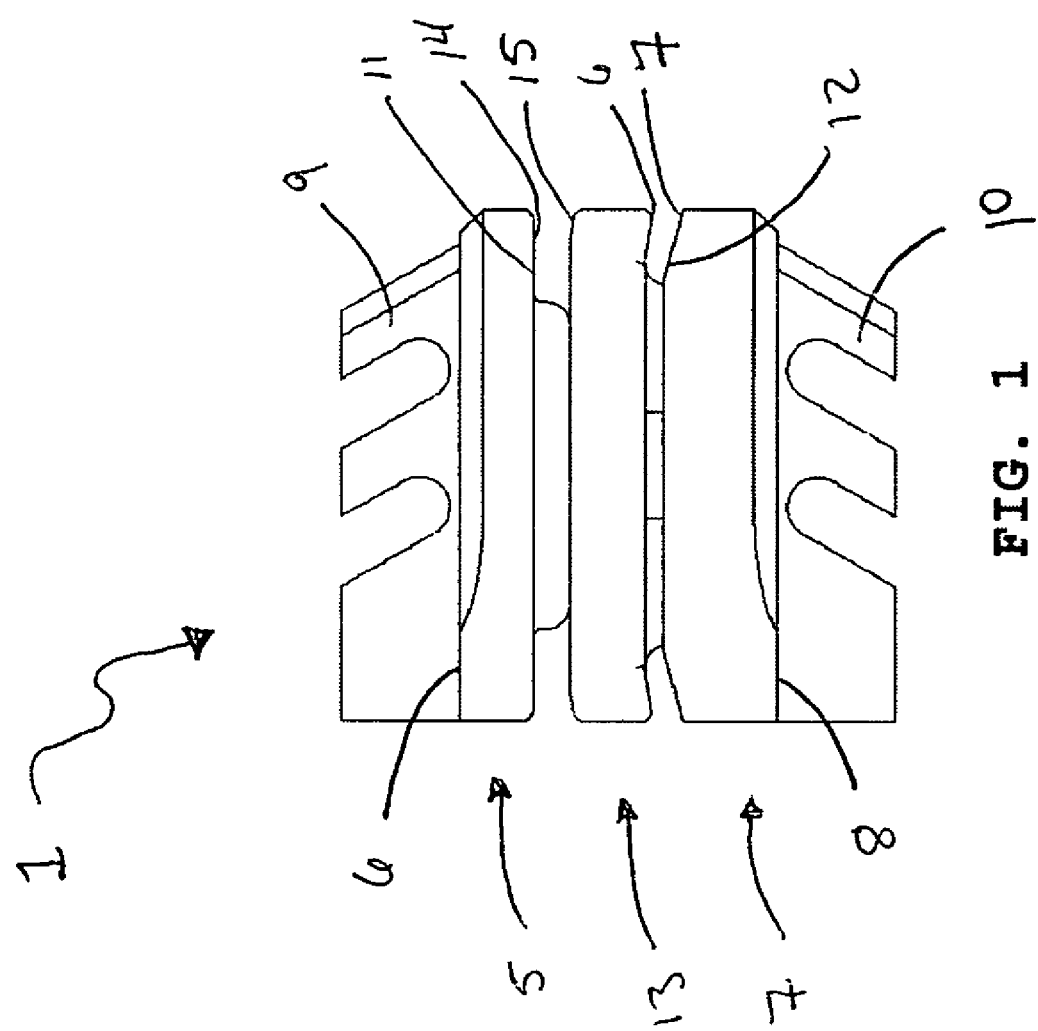
FIG. 1 is a side-view of an embodiment of a prosthetic disc design of the present invention.

The present invention relates generally to a prosthetic spinal disc for replacing a damaged disc between two vertebrae of a spine. The present invention also relates to a method for implanting a prosthetic spinal disc via anterior implantation. In particular, the present invention encompasses a method for implanting the prosthetic spinal disc via an anterior approach.

As described in detail below, the prosthetic spinal disc may be articulating or non-articulating.

Several embodiments of the invention illustrate different examples of how the interfacing surfaces of an articulating prosthetic disc may be formed. For instance, articulation may be accomplished with one interfacing surface, such as a ball and joint, or alternatively may be accomplished with two or more interfacing surfaces such as a core disposed between an upper and lower articulating surface. The configuration of the surface contact may vary to permit or restrict different types and ranges of motion of the treated area. Thus, the contact profile of the interfacing surface may be an area (such as with a ball and socket configuration), a line (such as with a roller or sleeve bearing), or a point (such as with a ball bearing).

The materials used for different embodiments of the invention will depend to some extent upon the type of surface contact being used as well as the type and extent of wear that may result. Examples of materials that may be used include, but are not limited to polyethylene (or other elastomeric material) on metal, metal on metal, or ceramic on ceramic.

The present invention also allows for customization of the instantaneous axis of rotation (IAR) and/or the center of rotation (COR) of one vertebral body with reference to another. The IAR and COR of a healthy vertebral body with respect to another is constantly changing in all planes because of pushing, pulling, and tethering of the segment through its range of motion by the ligaments, annulus, muscles, facets and other portions of the spine. Often, prosthetic disc replacement designs fail to mimic this varying IAR and COR. For example, a fixed ball and socket has a fixed IAR and COR. One potentially adverse result from using a prosthetic disc having a constrained implant is that the device may cause damage to facet joints due to anatomical interferences that may occur with a fixed axis of rotation. On the other hand, in general constrained IAR systems have been more stable than past designs utilizing a moving IAR. One example of a prosthetic disc having a fixed IAR is described in U.S. Pat. No. 5,314,477.

Conversely, past devices utilizing a moving IAR have provided the advantage of allowing for shear translation and of at least partially mimicking of the moving IAR of a healthy spine. These advantages, however, typically have been achieved in the past at the expense of a loss of stability of the device. Some examples of prosthetic disc designs having a moving IAR are described in U.S. Pat. Nos. 4,759,766, 5,401, 269, and 6,414,551.

In contrast, the present invention allows for an implant design that can mimic or partially mimic this varying IAR and COR to the extent desired by a physician while also preserving stability of the device. For example, one embodiment of the invention is a prosthetic disc that provides a moving IAR substantially in the sagittal plane so that a patient can more easily flex and extend the spine while limiting the movement of the IAR under lateral bending. It is believed that this configuration provides the best of both worlds by allowing a moving IAR for the predominant or more common motion a patient may undertake in day-to-day life while limiting lateral bending to achieve greater stability to the device. Several embodiments of the invention permit translation of one vertebral body with respect to another. By allowing for translation in the transverse plane, the disc designs results in the IAR and COR also translating in the transverse plane. As explained further below, one additional way of achieving a varying IAR and/or COR in three dimensional space is by combining two articulating surfaces opposing one another that can both translate with respect to each other in the transverse plane and rotate in other planes.

The interfacing surfaces of articulating and non-articulating embodiments of the present invention also allow for varying degrees of rotational and linear translation, and several embodiments of the present invention likewise permit a similar range of rotation and linear translation. Rotational translation is the movement of the intervertebral segment as a result of movement such as flexion, extension, and lateral bending. There are two components in this translation: one in the anterior/posterior direction and one in the transverse plane. Linear translation is translation in the transverse plane as a result of shear forces applied to the intervertebral segment. Thus, a ball and socket mechanism fixed in one location relative to the intervertebral segment would allow only rotational translation but would not permit linear translation. As illustrated in many of the embodiments that follow, however, linear translation of a ball and socket configuration could be achieved if the ball and socket were able to move in the transverse plane.

The present invention also contemplates the use of a prosthetic spinal implant that has a fixed IAR. For example, in one embodiment of the present invention comprises a two piece assembly design. Each assembly is comprised of a top and bottom endplate with interior surfaces that are curved. The surfaces contact each other and allow for rotation about the longitudinal axis of the spine as well as bending across the axial plane.

Endplates are used to associate the prosthetic disc with the vertebral bodies neighboring the disc. The endplates may be configured in several ways to help ensure a desired endplate-bone interface. For instance, the endplates may have one or more keels that extend into the bony portion of the vertebral body. Over time, bony ongrowth/ingrowth will surround the endplate and further help secure the endplate to the vertebral body.

In addition to keels, the endplate may have other or additional geometry that helps securely hold the endplate in place. For example, the end plate may have one or more teeth, rails, ribs, flanges, or other configurations that can help provide a surface that can secure the endplate more readily to the bone. Other short-term fixation may include screws or other fasteners that hold the end plate to the vertebral body. In some embodiments, these fasteners may be removed once a more long-term interface has been established, or alternatively the fasteners may remain in place indefinitely or until the prosthetic disc needs adjustment and/or replacement.

In addition to providing an endplate surface geometry or configuration that may promote bony ongrowth/ingrowth to hold the interfacing surfaces together securely over the long term, these configurations also may help provide short term fixation of the endplate to the vertebral body. For example, a keel may have a wedge shape so that the width of a first end of the keel near the endplate is narrower than the width of the distal end. Once installed, the inverted wedge of the keel helps prevent separation of the endplate from the vertebral body at least until bony ongrowth/ingrowth can more securely hold the endplate in place.

To help accelerate and to further promote bony ongrowth/ingrowth at the interface between the vertebral body and the end plate, the end plate may be coated with an osteoconductive material and/or have a porous or macrotexture surface. For example, the end plate may be treated with a coating that promotes bone growth. Examples of such coatings include, without limitation, hydroxyl appetite coatings, titanium plasma sprays, sintered beads, or titanium porous coatings.

FIG. 1 is a side view of a prosthetic spinal disc 1 which may be located between sequentially aligned vertebral bodies, such as are found in the cervical, thoracic, and lumbar spine. Prosthetic spinal disc 1 conforms in size and shape with the spinal disc that it replaces and restores disc height and the natural curvature of the spine. Prosthetic spinal disc 1 comprises two opposite end plate 5 and 7 which are disposed in two substantially parallel horizontal planes when it is at rest, i.e., when it is not subjected to any load, either moderate or heavy.

Outer faces 6 and 8 of end plates 5 and 7 are in direct contact with vertebral bodies (not shown) and may be textured or have a plurality of teeth to ensure sufficient contact and anchoring to the vertebral bodies. Outer faces 6 and 8 of end plates 5 and 7 may also have a porous or macrotexture surface that facilitates bone ongrowth/ingrowth so that the prosthetic spinal disc 1 is firmly affixed to vertebral bodies. Outer faces 6 and 8 of end plates 5 and 7 may also have keels 9 and 10 that may fit into channels in the vertebral bodies to facilitate anchoring. Disposed between the inner faces 11 and 12 of end plates 5 and 7 is a core 13, which is securely placed between the inner faces of end plates 5 and 7. A stop member 15 is formed around the equator of the core 13, which functions to limit the motion of vertebral bodies beyond a predetermined limit that is deemed unsafe to the patient.

As shown in FIG. 1, mechanical stops may be designed as part of the upper and lower endplates 5 and 7 and core 13. In this embodiment, the mechanical stop results as a function of the design of the upper and lower endplates 5 and 7 and the design of the core 13. For example and with continuing reference to FIG. 1, upper endplate 5 is designed with a first contact surface 14 on the interior surface 11 of the upper endplate 5. Core 13 is designed with a second upper contact surface 15. During flexion and/or extension, first contact surface 14 may abut or come into contact with second contact surface 15, thus effectively limiting the degree of movement allowed by the articulating surfaces. Similarly, the core is designed with a lower third contact surface 16 while lower endplate is configured with an upper fourth contact surface 17. During extension and/or flexion, third contact surface 16 may abut or come into contact with fourth contact surface 17, thus effectively limiting the degree of movement allowed by the articulating surfaces. Contact surfaces 14, 15, 16, and 17 may be formed with various slopes, angled surfaces, and thickness to specify the degree of movement permitted by the disc design.

Figure 3:
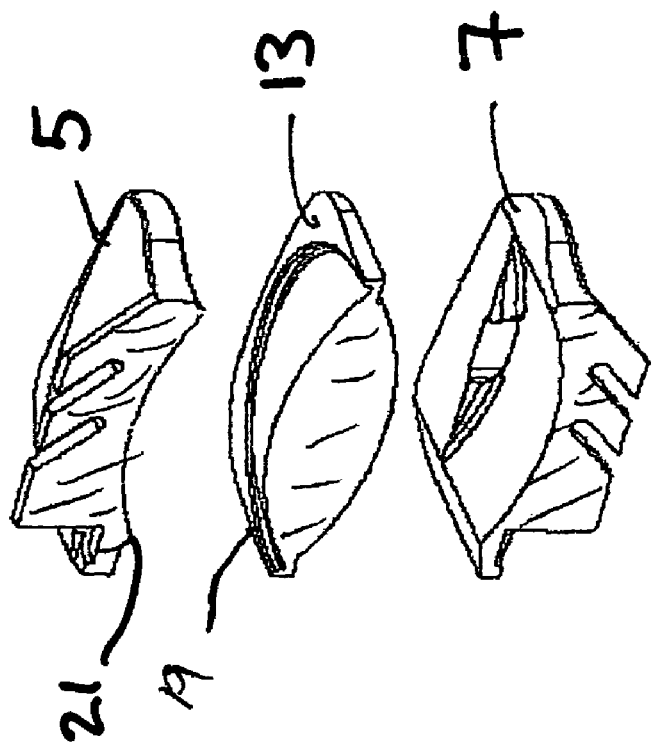
FIG. 3 is a cross sectional view of an embodiment of a prosthetic disc design of the present invention.
Figure 2:
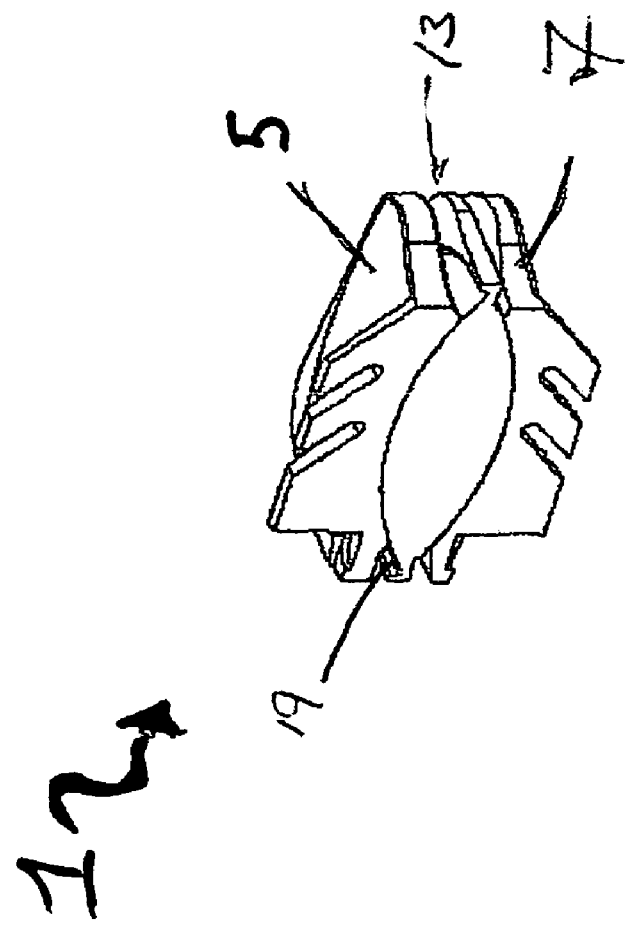
FIG. 2 is a cross sectional view of an embodiment of a prosthetic disc design of the present invention.

In an alternative embodiment, the stop member may be formed from a ridge of material disposed about the partially spherical surface of the core above the equatorial plane of core 13. As seen in FIGS. 2 and 3, a cross sectional view of an embodiment of the prosthetic disc is shown. Prosthetic disc 1 has an upper endplate 5, lower endplate 7 and core member 13 disposed there between. As seen in FIGS. 2 and 3, core member is formed with a lip or rim 19 that serves as a stop member. As end plate 5 moves relative to core 13 in response to movement of the spine, stop member 19 may approach or engage with end plate 5 to restrict further motion in a particular direction. Endplate 5 may be configured with a raised edge that mates or abuts with the stop member 19 of core member 13. Stop member 19 may be formed of a relatively rigid material so that additional motion is substantially prevented once engaged against an end plate. Alternatively, the stop material may be made of resilient material that provides some cushioning or flex from deformation of the stop material before the range of motion is fully limited.

In alternative embodiments, stop member 19 may be disposed on one or more of end plates 5 and 7. For instance, end plates 5 and 7 may be configured with raised areas or ridges on its perimeter that engage with either core 13 or an opposing end plate in order to limit further motion in a particular direction. Any of the stop members discussed above may be designed to limit motion to a greater degree in one direction than in another. Thus, the stop member may have various shapes and thicknesses to provide a variable range of motion that favors or disfavors movement in particular planes. For example, the stop member may have increased thickness on the side portion of the core to provide a more limited range of lateral motion of the spine while still allowing motion in the posterior/anterior direction.

The motion segment comprises a anterior prosthetic spinal disc 1 and adjacent upper and lower vertebral bodies. The exact contours of core 13, inner surfaces of endplates 5 and 7 and stop member 19 determine the range of motion allowed in flexion and extension, side bending, shear and rotation.

It is preferred that anterior prosthetic spinal disc 1 closely mimics the mechanical functioning and the various physical attributes of the natural spinal disc that it replaces. In some instances, however, the prosthetic spinal disc may permit a more limited range of motion in one or more directions in order to prevent further spinal injury. In general, the prosthetic spinal disc can help maintain the proper intervertebral spacing, allow for proper range of motion, and provide greater stability. It can also help transmit physiological stress more accurately.

End plates 5 and 7, core 13, and stop 19 may be composed of a variety of biocompatible materials, including metals, ceramic materials and polymers. Such materials include, but are not limited to, aluminum, cobalt-chromium, alloys, and polyethylene. Outer surfaces 6 and 8 of the end plates 5 and 7 may also contain a plurality of teeth, maybe coated with an osteoconductive material, antibiotics or other medicament, or may have a porous or macrotexture surface to help rigidly attach the end plates to the vertebral bodies by promoting the formation of new bony ongrowth/ingrowth. Such materials and features may be used in any of the anterior prosthetic spinal discs described herein.

Figure 4:
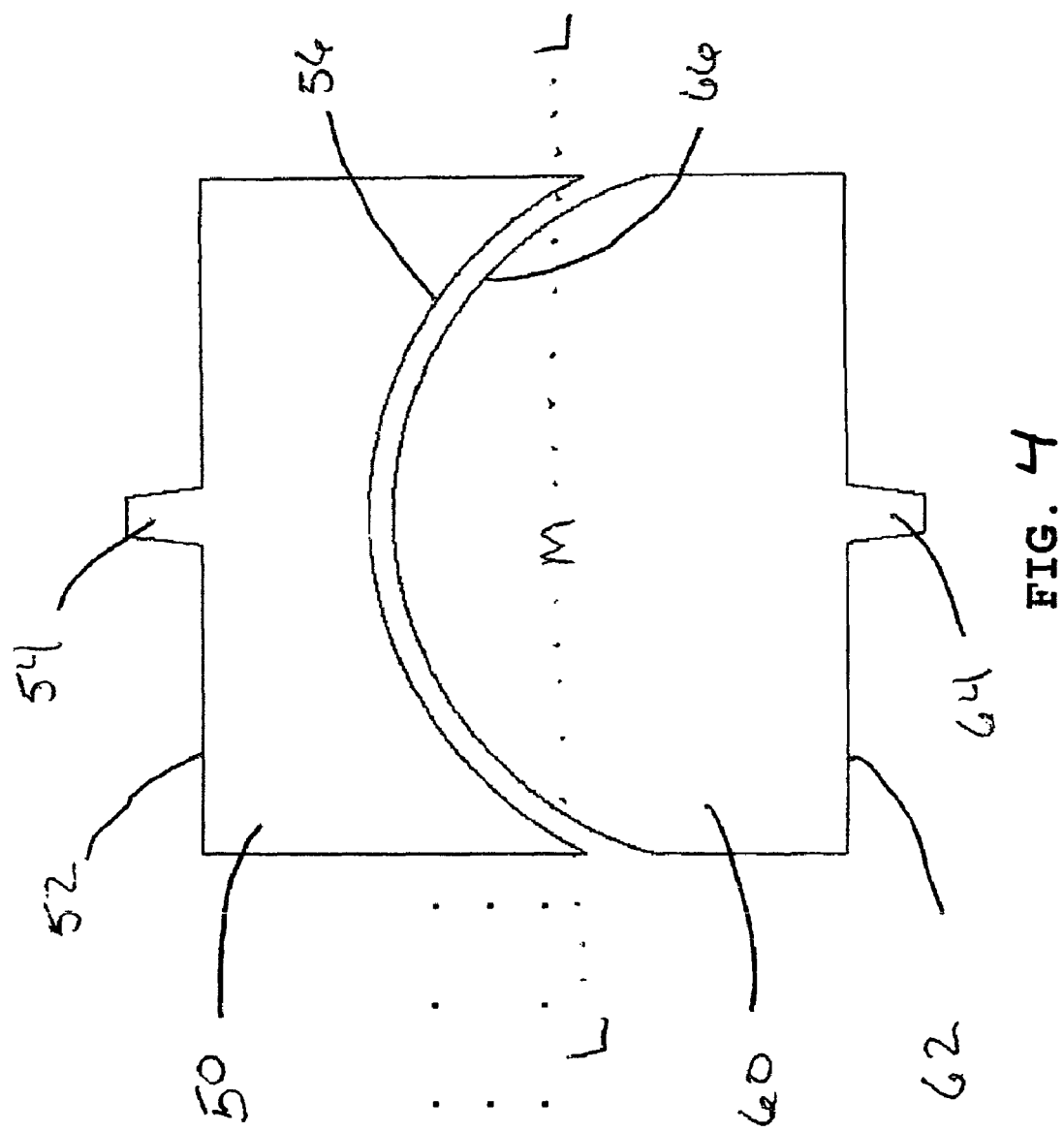
FIG. 4 is an medial-lateral view of an embodiment of a prosthetic disc design of the present invention.
Figure 5:
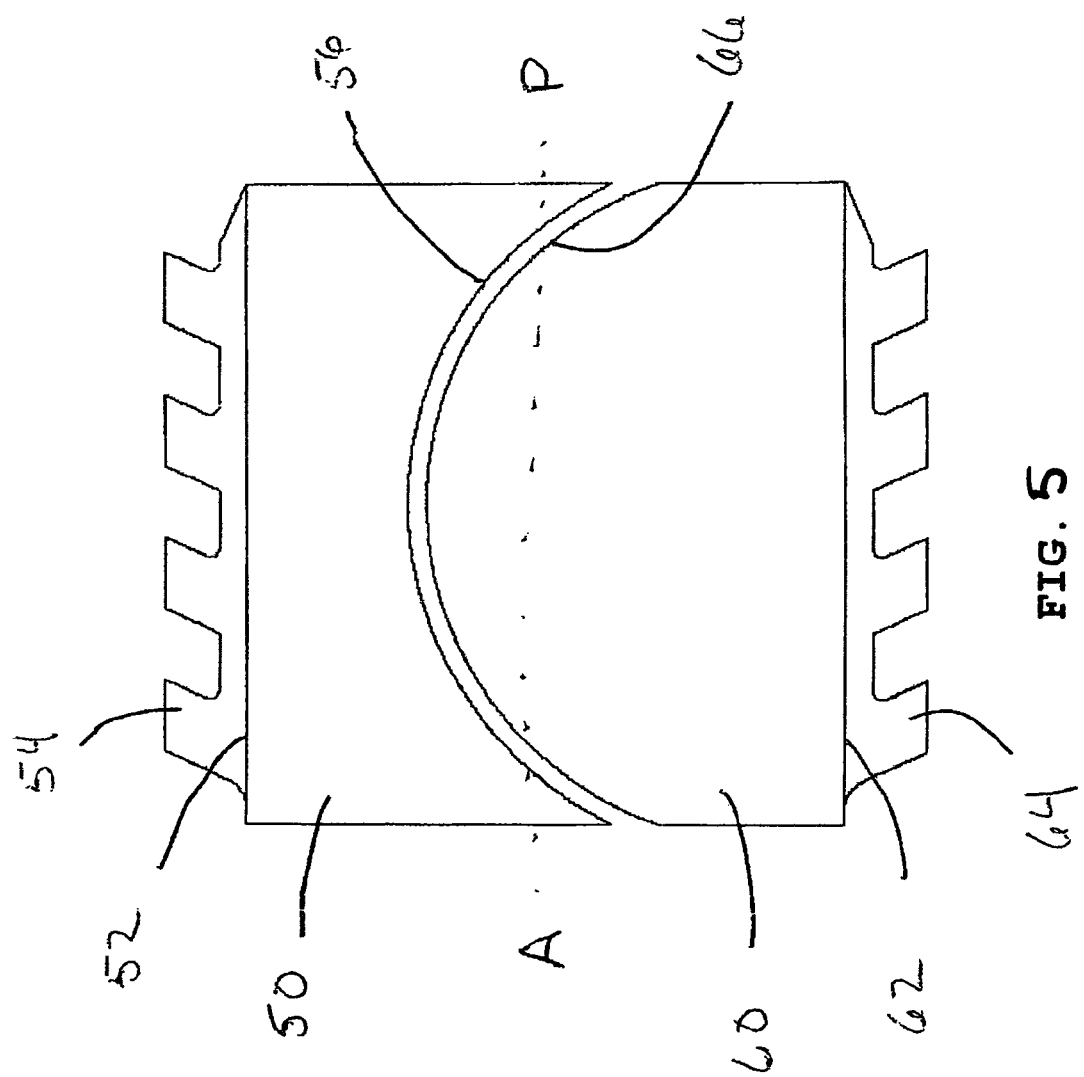
FIG. 5 is an anterior-posterior view of the embodiment of FIG. 4.

FIGS. 4-8 illustrate various embodiments of the invention including contacting surfaces that complement each other to form an arced or curved surface in the medial-lateral direction and in the anterior-posterior direction. FIG. 4 illustrates the curvature created in the medial-lateral direction (designated L-M-L), while FIG. 5 shows the curvature created in the anterior-posterior (designated A-L) direction. As shown in FIG. 4, first endplate 50 has an outer surface 52 that contacts a vertebral body (not shown). Second endplate 60 has an outer surface 62 that contacts a vertebral body (not shown). The outer surfaces of first endplate 50 and second endplate 60 are configured with keels 54 and 64 respectively, that may be inserted into the vertebral bodies. FIG. 4, shows the inner surfaces 56, 66 of the first and second endplates respectively configured to create a curve. When viewed in the medial-lateral direction, the curved surfaces 56, 66 of the first and second endplates 50 and 60 allow the vertebral bodies (not shown) to move relative to each other in the medial-lateral direction. As shown in FIG. 5, first endplate 50 has an outer surface 52 that contacts a vertebral body (not shown). Second endplate 60 has an outer surface 62 that contacts a vertebral body (not shown). The outer surfaces of first endplate 50 and second endplate 60 are configured with keels 54 and 64 respectively, that may be inserted into the vertebral bodies. FIG. 5, shows inner surfaces 56, 66 of the first and second endplates 50 and 60 respectively configured to create a curve. When viewed in the posterior-anterior direction, the curved surfaces 56, 66 of the first and second endplate allow the vertebral bodies (not shown) to move relative to each other in the posterior-anterior direction.

The implants may be configured according to a variety of factors such as the size of the vertebral bodies, the loading that the implants will undergo, and the range of motion desired. Also, while permitting movement to mimic or partially mimic the natural movement of the spine, it may be desirable that prosthetic discs be designed to maintain a distance between the vertebral bodies that approximate the height of a natural disc. These design considerations may be accomplished in any number of ways. For example, one aspect of the design of the implants that may vary is the radius of curvature. The radius of curvature may be varied between implant designs to accommodate different ranges of motion. For example, changes in the design of the radius of curvature of the articulating surfaces of the endplates allow the designer of the implant to vary the range and/or type of motion the implant will allow. In other embodiments, the height of the implants may be varied. Accordingly, changes in the thickness of one or more of the endplates allow the designer of the prosthetic disc to accommodate different spacing between the two vertebral bodies. Preferably, the height of the superior or upper endplate is designed to provide the height preferences of any particular embodiment. Accordingly, a surgeon may be provided with a kit comprising one inferior endplate and several superior endplates. While the articulating surfaces of each superior endplate fits with the inferior endplate, the surgeon may select from various superior endplates of differing thickness to tailor the implanted prosthetic disc to approximate each individual's own ideal or natural disc height. In disc designs comprising a three component design, namely, two endplates and a central core member, alternative embodiments contemplate providing a surgeon with endplates of fixed height and various core members of differing heights. Thus, the surgeon may select a core member to achieve the desired spacing once the disc is implanted into a patient.

Figure 6:
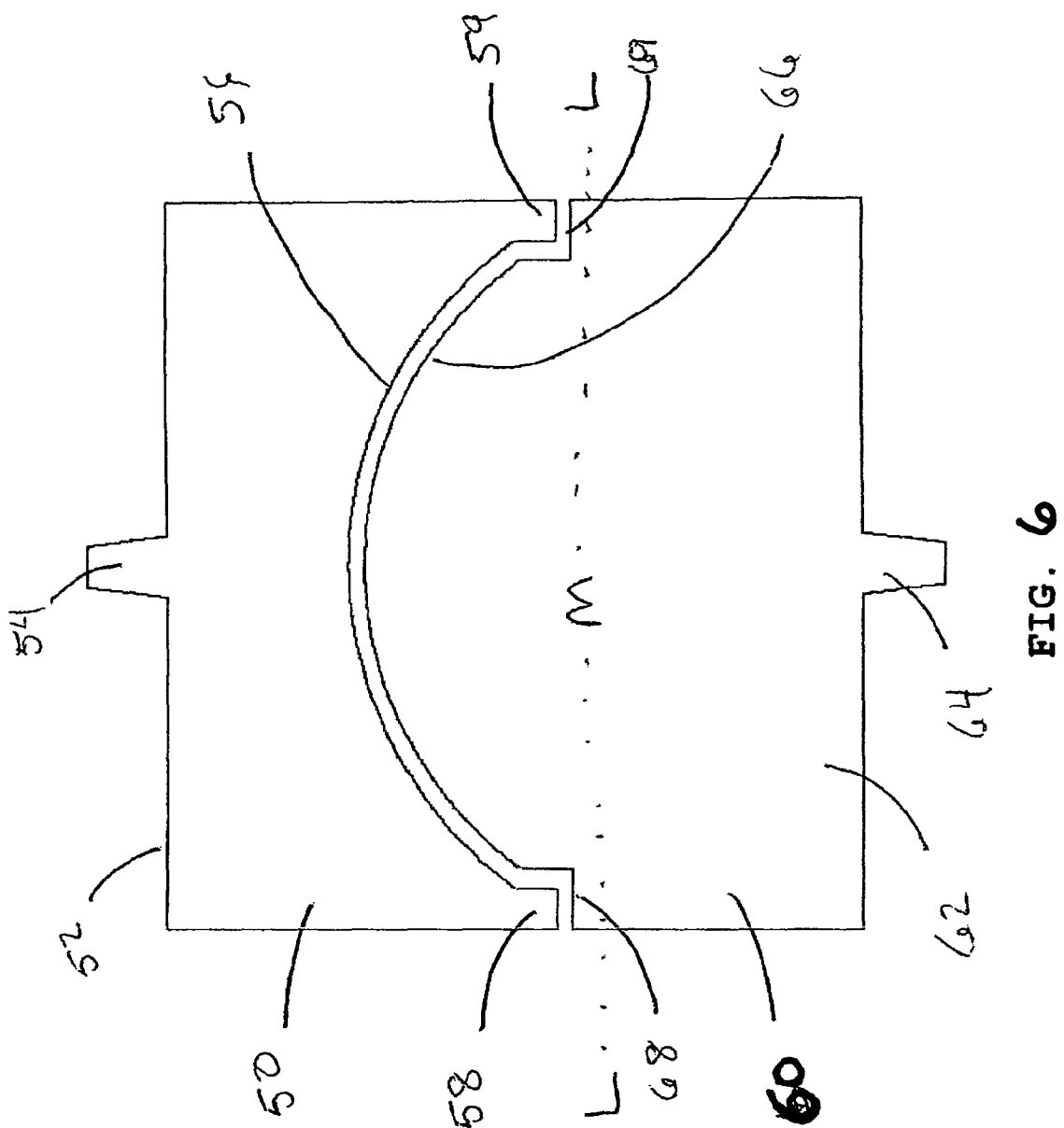
FIG. 6 is an medial-lateral view of an embodiment of a prosthetic disc design of the present invention.
Figure 7:
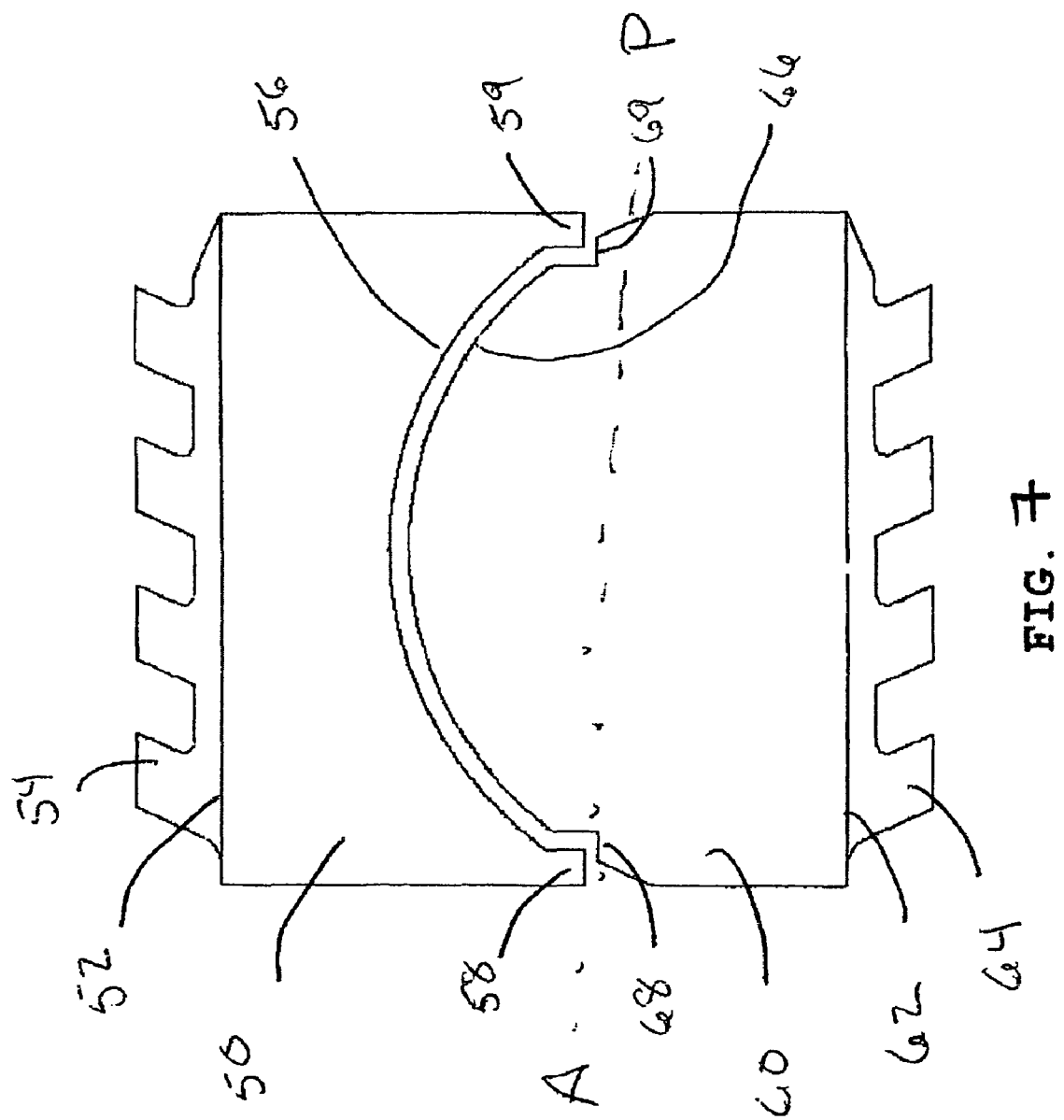
FIG. 7 is an anterior-posterior view of the embodiment of FIG. 6.

Referring to FIGS. 6 and 7, which are similar in orientation to FIGS. 4 and 5, the upper and/or lower portions of the implants may have stops to help limit motion in one or more directions. As shown in FIG. 6, for example, medial-lateral movement can be controlled or limited by including stops 58 and 59 on both sides of lower surfaces 56 of endplate 50. As shown in FIG. 6, the opposing surfaces 68 and 69 of endplate 60 is designed to engage stops 68 and 69, preventing further movement in the direction restricted. Alternatively, a resilient material may be disposed between stop 58 an 59 and opposing surfaces 68 and 69 in order to provide cushioning and to allow resistance to further movement to increase progressively. FIG. 7 illustrates that stops 58 and 59 may be similarly used on one or more sides of the implant to limit the range of motion in the anterior-posterior direction. While the stops in FIGS. 6 and 7 are illustrated protruding upwards or downwards, other configurations also may be used to create a stop or to limit motion. For instance, the sliding surface of the portions of the implants may be prevented from further movement simply by contacting the end plate of the opposing portion.

Figure 8:
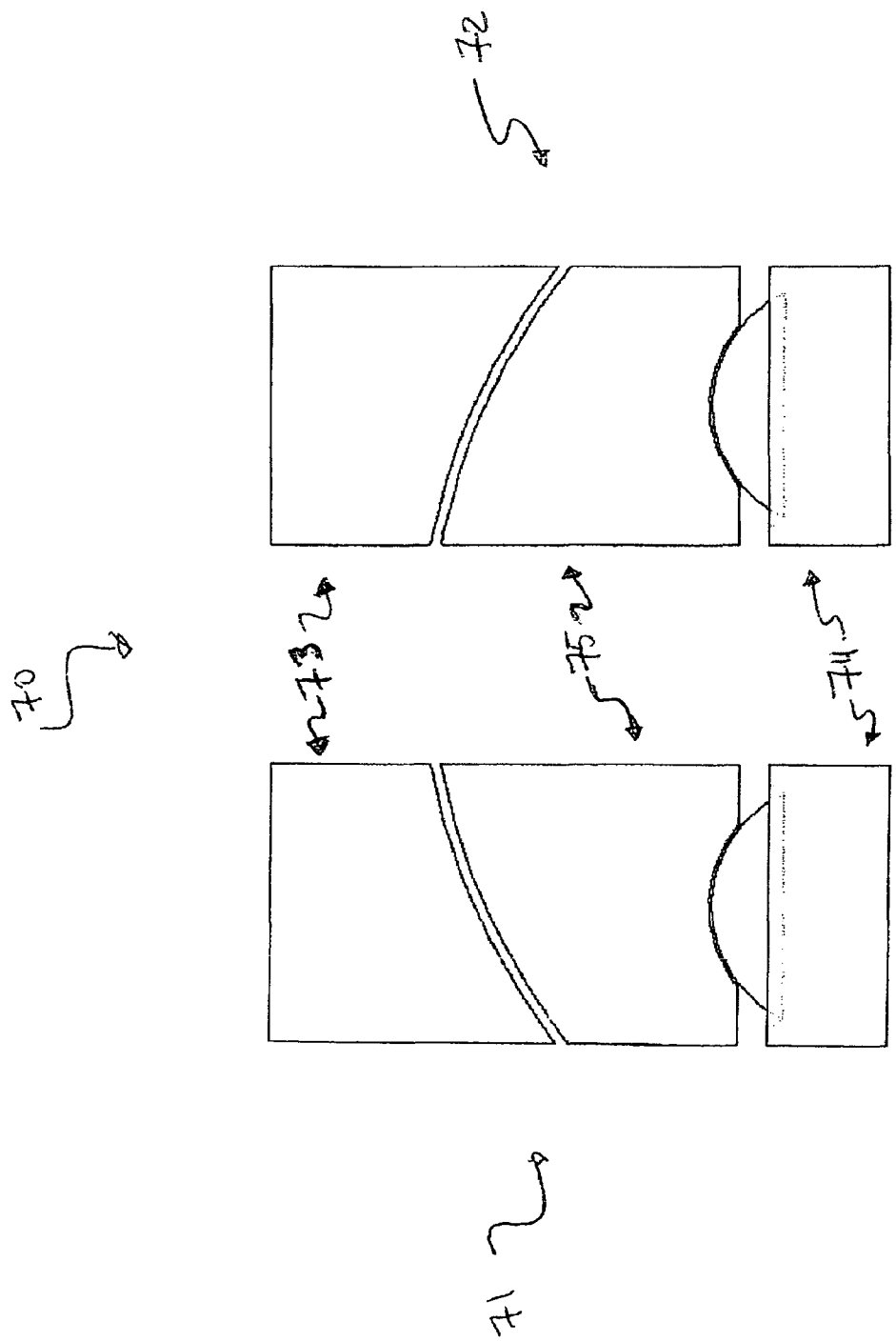
FIG. 8 is an illustration of an embodiment of the prosthetic disc design of the present invention.

FIG. 8 illustrates one embodiment of the invention where different surfaces of the prosthetic disc provide for different types of movement. In FIG. 8, prosthethic disc 70 comprises two assemblies 71 and 72, each assembly comprised of endplates 73 and 74, and a core member 75 disposed between the endplates 73 and 74. In this embodiment of the present invention, the articulating surfaces between upper endplates 73 and upper surfaces of the core member 75 are configured to permit only lateral bending. The radius of curvature of the articulating surfaces is designed to provide a uniform contact area between the upper endplates 73 and the core members 75, with the dimensions of the radius being dependent on the final spacing of the two assemblies 71 and 72. The articulating surfaces between the lower endplates 74 and lower surface of the core member 75, are configured to with a ball and socket interfacing configuration or radiused rail configuration that allows for axial rotation.

Figure 9:
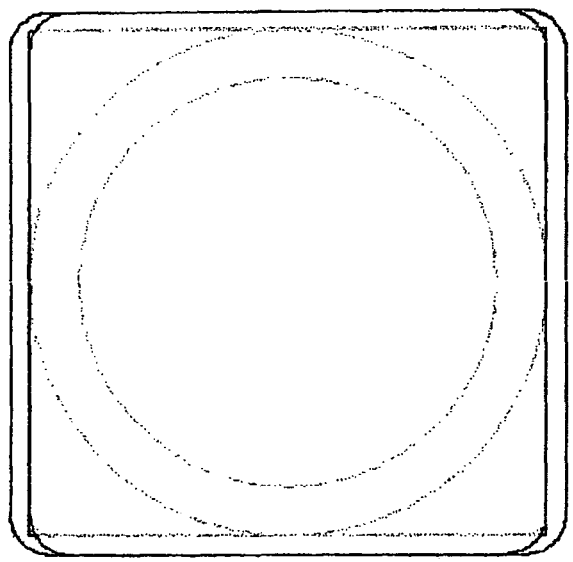
FIG. 9 is an illustration of an embodiment of the prosthetic disc design of the present invention.
Figure 11:
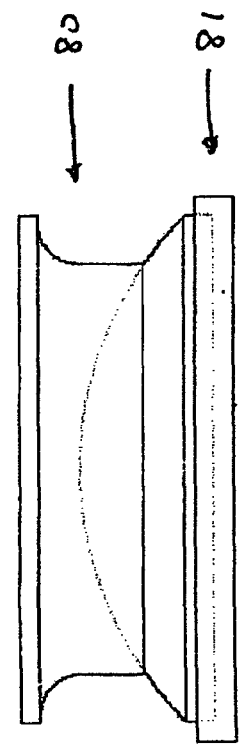
FIG. 11 is an illustration of an embodiment of the prosthetic disc design of the present invention.
Figure 10:
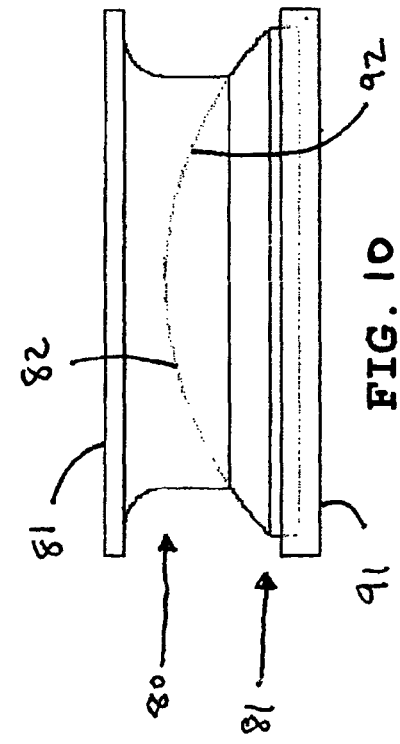
FIG. 10 is an illustration of an embodiment of the prosthetic disc design of the present invention.

One example of the present invention is illustrated in FIGS. 9-11. In this embodiment of the present invention, a prosthetic disc configured with a fixed IAR is shown. The prosthetic disc is comprised of two endplates 80 and 90. In this embodiment the endplates are shown without the keels previously described, although in alternative embodiments, they may be present. First endplate 80 has an upper surface 81 and lower surface 82. Second endplate 90 has lower surface 91 and upper surface 92. In this embodiment, lower surface 82 of first endplate 80 directly engages upper surface 92 of second endplate 90. Lower surface 82 and upper surface 92 of endplates 80 and 90 are configured such that they are substantially spherical in curvature and have substantially the same radius of curvature. This design allows the interacting surfaces to contact over an area as opposed to a line or point.

While the discussion relating to FIGS. 4-7 relate to two component designs, i.e. an upper and lower endplate with articulating surfaces, it would be apparent to one of skill in the art that each of the preceding designs may be comprised of a three component design, i.e. with a core element disposed between the upper and lower endplates.

Accordingly, prosthetic disc designs of the present invention may also comprise three component parts: an upper rigid plate, a lower rigid plate, and a central core or core element. The core element is disposed generally between articulating surfaces of the upper and lower plates. The articulating surfaces of each plate may be contoured to provide a desired range of motion. For example, one or more of the articulating surfaces may have a substantially spherical curvature. In this manner, the articulating surface may generally correspond to a portion of a ball or a socket. The central element may likewise have a contoured surface that generally has the same curvature as the articulating surface it contacts. Thus, a spherical-shaped articulating surface can receive or contact a portion of the central element having a spherical contour having a similar radius of curvature. The contact between the two surfaces may therefore correspond to a portion of a ball and socket.

Providing a spherical surface allows the two components to rotate and slide across the contacting surfaces in a manner that would permit bending and rotation of one vertebral body relative to another. If these two contacting surfaces were the only elements allowing movement, the IAR of the disc would be fixed. In some embodiments, a second contacting surface is provided. The second contacting surface allows the disc to mimic a variable IAR of a healthy disc. For example, a second contacting surface between the second rigid plate and the central element may have a cylindrical contour, preferably allowing the core element to provide rotation in the anterior-posterior direction. Thus, it is preferred that the cylindrical surfaces of the second rigid plate and core element have an axis of rotation that extends approximately in a lateral direction.

The combination of a spherical shaped surface contact between one plate and a portion of the core element with a second generally cylindrical contacting surface between another plate and another portion of the core element allows the disc to have a variable IAR. This configuration also allows for translation of one vertebral body relative to another vertebral body without requiring either vertebral body to rotate and without requiring the distance between the vertebral bodies to increase or decrease.

Figure 12:
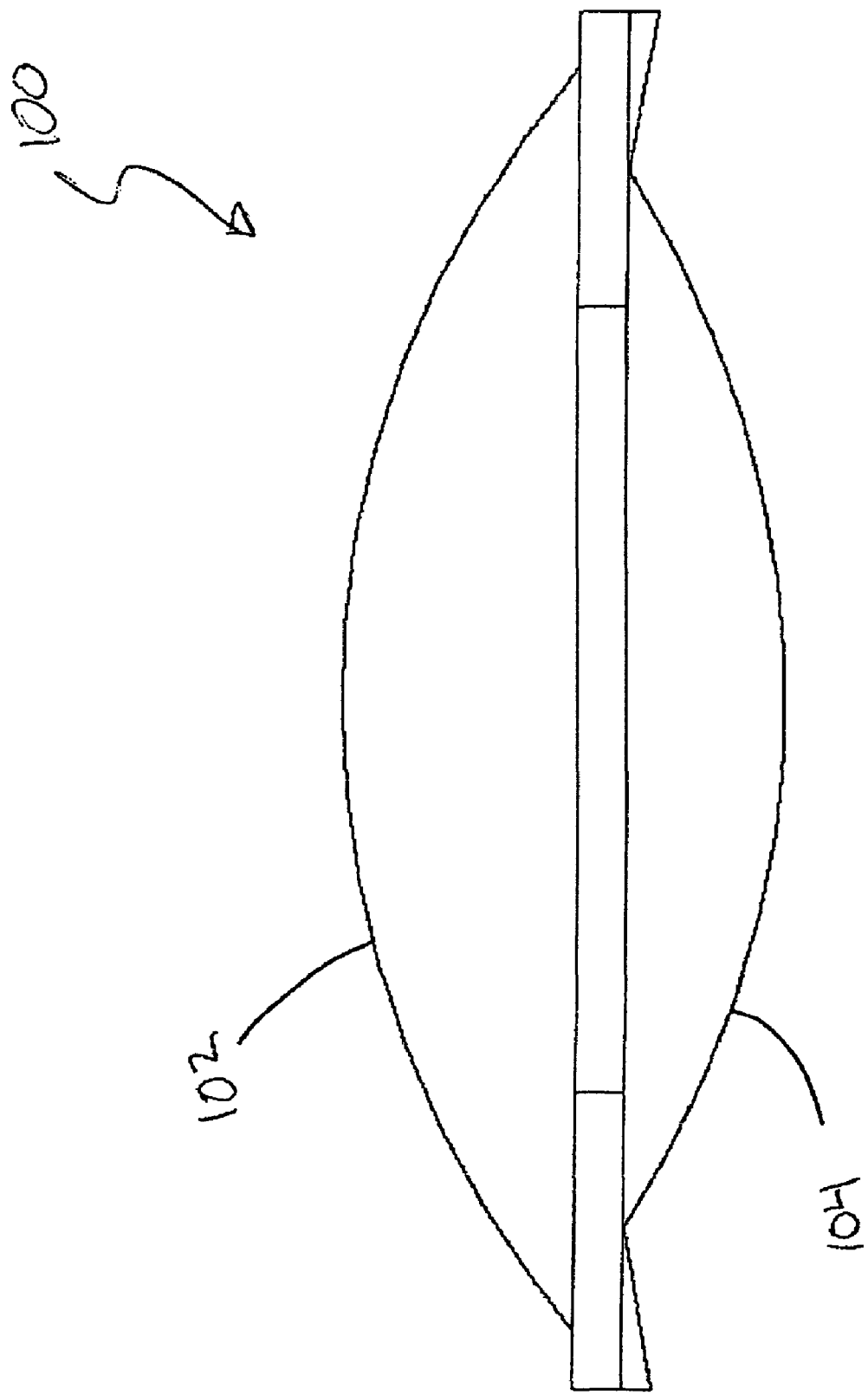
FIG. 12 is an illustration of one embodiment of a central core member.

The curvature of the articulating surfaces of the plates may be concave and the corresponding contoured portions of the core element may be convex to provide contact between the surfaces. For example, in one embodiment as shown in FIG. 12 core element 100 may have a contoured convex surface 102 that it semi-spherical or generally corresponds to a portion of a spherical surface, and a contoured convex surface 104 that is semi-cylindrical or generally corresponds to a portion of a cylinder. Alternatively, one or more of the contoured surfaces of the core element may be concave and the articulating surface for which it engages likewise may be inverted. For example, in one embodiment core element may have a contoured convex surface that it semi-spherical or generally corresponds to a portion of a spherical surface, and a contoured concave surface that is semi-cylindrical or generally corresponds to a portion of a cylinder. One advantage of this configuration is that it may be capable of achieving a lower overall height than a core element having two convex contoured surfaces.

It is preferred that the contact between the articulating surface of a plate and a contoured surface of a core element extends over an area rather than a line or a point. More preferably, all contact surfaces of the invention extend over an area. However, if a convex semi-spherical surface were formed with a smaller radius of curvature than the corresponding concave surface, it would be possible to have the contact between the two surfaces correspond to a point contact. Likewise, a convex cylindrical surface may be formed to be smaller than the concave cylindrical surface it engages with in order to form a contact surface corresponding to a line.

The following examples further illustrate how several of the features described above may be implemented in a prosthetic disc.

Figure 13:
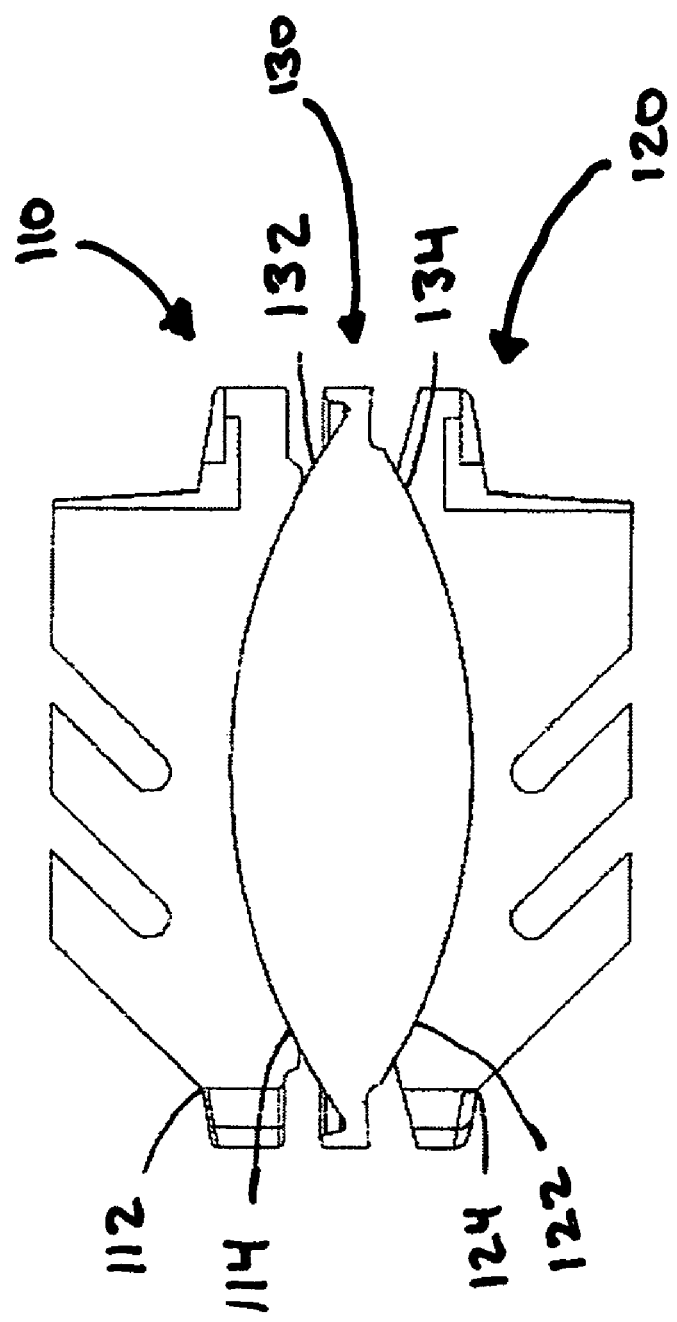
FIG. 13 is an illustration of an embodiment of the prosthetic disc design of the present invention.

In one embodiment of the present invention, a three component prosthetic disc is provided. As seen in FIG. 13, the prosthetic disc is comprised of a first endplate 110, a second endplate 120, and a central core 130. First endplate 110 has upper surface 112 and lower surface 114. The second endplate 120 has upper surface 122 and lower surface 124. Central core 130 has upper surface 132 and a lower surface 134. While this particular embodiment is described with surfaces that have certain orientations, it should be understood that the surfaces described may be placed on an upper or lower component and that the invention is not restricted or limited to the orientations described.

The components may be designed with interacting surfaces that allow for different types of movement. For example, the lower surface of the first endplate and upper surface of the central core may be designed as substantially spherical surfaces. The interaction between the lower surface of the first endplate and the upper surface of the central core, thus occurs over an area. The interacting surfaces allow the surfaces to move with respect to each other in three directions: rotationally, medial-laterally, and in the anterior posterior direction. The interaction between the upper surface of the second endplate and the lower surface of the central core may be different. For example, the upper surface of the second endplate and the lower surface of the central core may be substantially cylindrical in shape. The two cylindrical surfaces permit rotational movement essentially in one direction (i.e. about one axis). Preferably, the radii of curvature of both cylindrical shapes are approximately the same such that the surface contact is over an area instead of a line. In this manner, the cylindrical surface can be configured to permit bending while restricting rotation. Thus, during flexion or extension both interface surfaces permit movement and result in a moving IAR.

In an alternative embodiment, the contacting surfaces may be designed to limit movement. For example, the upper surface of the core element and lower surface of the endplate may be substantially spherical in shape yet only allow rotational movement. In this embodiment of the present invention, the endplates and core elements are designed to limit the first contacting surfaces from moving in the medial lateral direction or anterior posterior direction.

In an alternative embodiment, a second cylindrical interfacing surface can be substituted for the spherical surface. This second cylindrical interfacing surface may be disposed orthogonally to the direction of the first cylindrical interfacing surface. In this manner, one surface will permit motion in one direction, such as flexion and extension, while the second will permit lateral bending.

Figure 15:
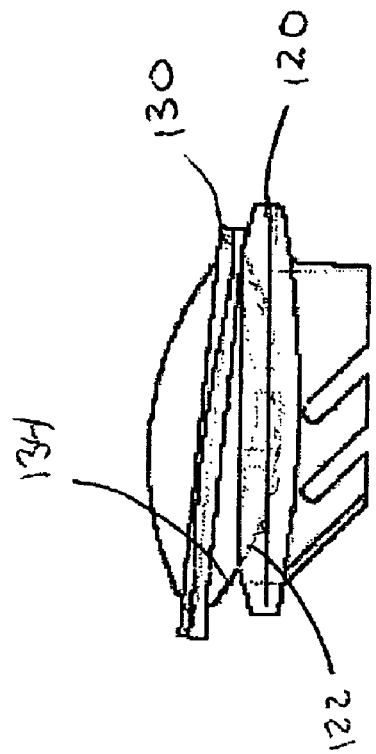
FIG. 15 is an illustration of a core member and bottom endplate in an embodiment of the present invention.
Figure 14:
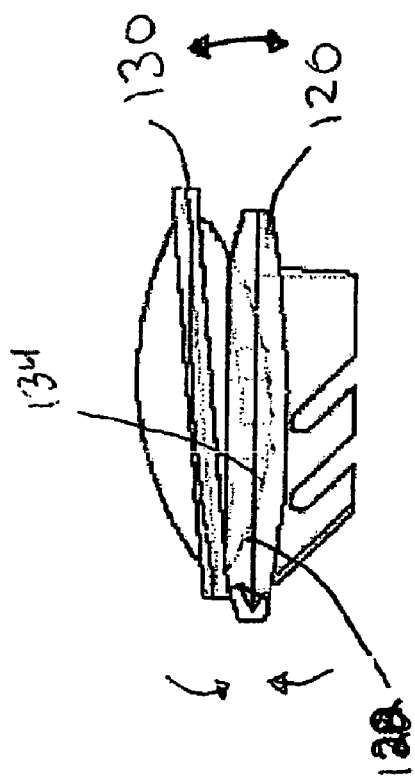
FIG. 14 is an illustration of a core member and bottom endplate in an embodiment of the present invention.

FIGS. 13-19 illustrate the types of motion that may be achieved using a first interfacing surface that is generally spherical and a second interfacing surface that is generally cylindrical. FIG. 13 illustrates a disc disposed in a neutral position having a disc height H. The prosthetic disc of the present embodiment is capable of mimicking or partially mimicking natural movement. For example, FIG. 14 shows lower endplate 120 and central core member 130 of an anterior prosthetic disc during extension. As can be seen in FIG. 13, articulation between upper surface 122 of lower endplate 120 and lower surface 134 of central core 130, allow for extension of the spine. As the articulating surfaces, i.e. upper surface 122 of lower endplate 120 and lower surface 134 of core element 130, in this embodiment are partially cylindrical in shape, the rotation allowed by articulating surfaces 122 and 134 allow rotation substantially in the posterior-anterior direction only. FIG. 15 shows the relative position of the central core 130 and lower endplate 120, during the opposite motion shown in FIG. 14, i.e. flexion.

Figure 16:
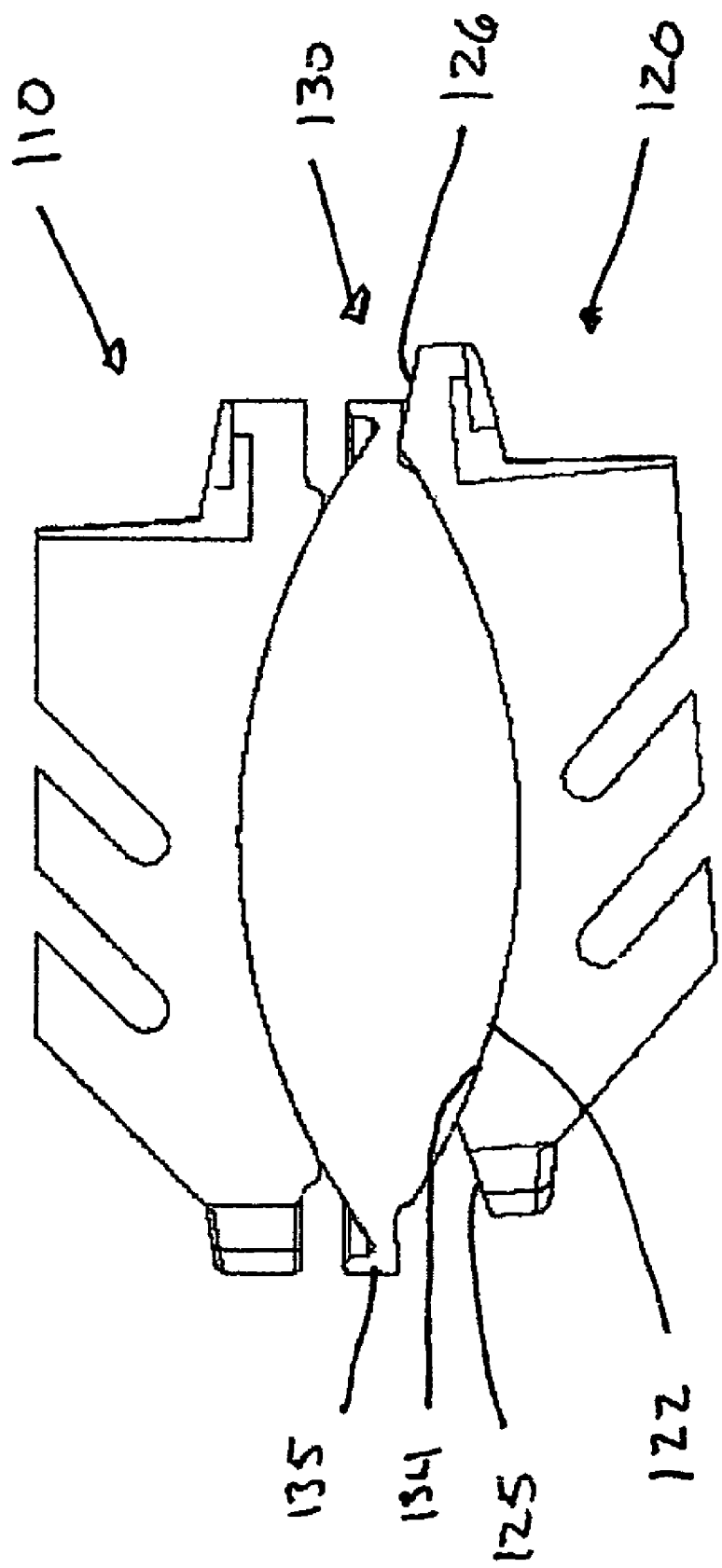
FIG. 16 is an illustration of an embodiment of the prosthetic disc design of the present invention.
Figure 17:
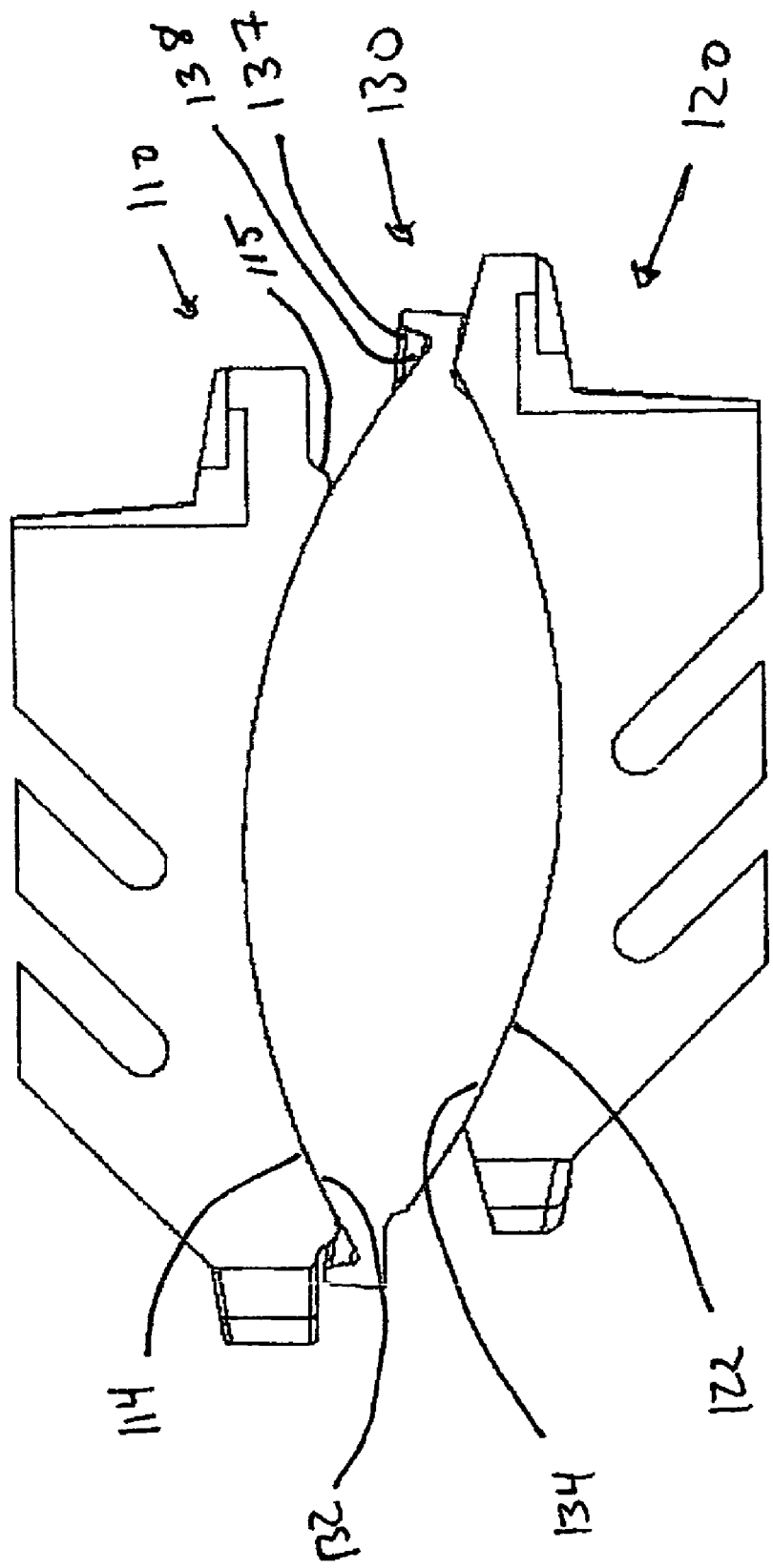
FIG. 17 is an illustration of an embodiment of the prosthetic disc design of the present invention.

In addition to the rotation allowed by the partially cylindrical articulating surfaces between the lower endplate and central core member in the posterior-anterior direction, the present embodiment also allows for translation in the anterior-posterior direction. As shown in FIGS. 16 and 17, the present embodiment is capable of translation during flexion. For example, FIG. 16 shows the relative position of the three components, i.e. upper endplate 110, lower endplate 120, and central core member 130, of a prosthetic disc during flexion. As can be seen in FIG. 16 and as previously described with respect to FIGS. 14 and 15, partially cylindrical upper surface 122 of lower endplate 120 and lower surface 134 of the central core member 130, allow the vertebral bodies (not shown) to rotate substantially in the anterior-posterior direction. In FIG. 16, rotation is in the anterior direction relative to the prosthetic disc's neutral position (shown in FIG. 13). FIG. 17 illustrates the relative positions of the three components of a prosthetic disc, i.e. upper endplate 110, lower endplate 120, and central core member 130, during both flexion and translation. As can be seen in FIG. 17, the prosthetic disc is in flexion, i.e. rotation in the anterior direction along the upper surface 122 of the lower endplate 120 and lower surface 134 of central core member 130. In addition to rotation in the anterior-posterior direction, FIG. 17 shows the relative position of the components of the prosthetic disc during translation. As FIG. 17 illustrates, partially spherical surface 114 of upper endplate 110 and partially spherical surface 132 of core member 130 are designed to allow upper endplate 110 to translate with respect to central core member 130. FIG. 17 illustrates the relative position of the components of a prosthetic disc during translation in the posterior direction. Because endplates 110 and 120 are attached to vertebral bodies, the ranges of motion capable by the prosthetic disc allow the vertebral bodies to move in the same direction, hence, mimicking or partially mimicking natural disc movement.

Figure 18:
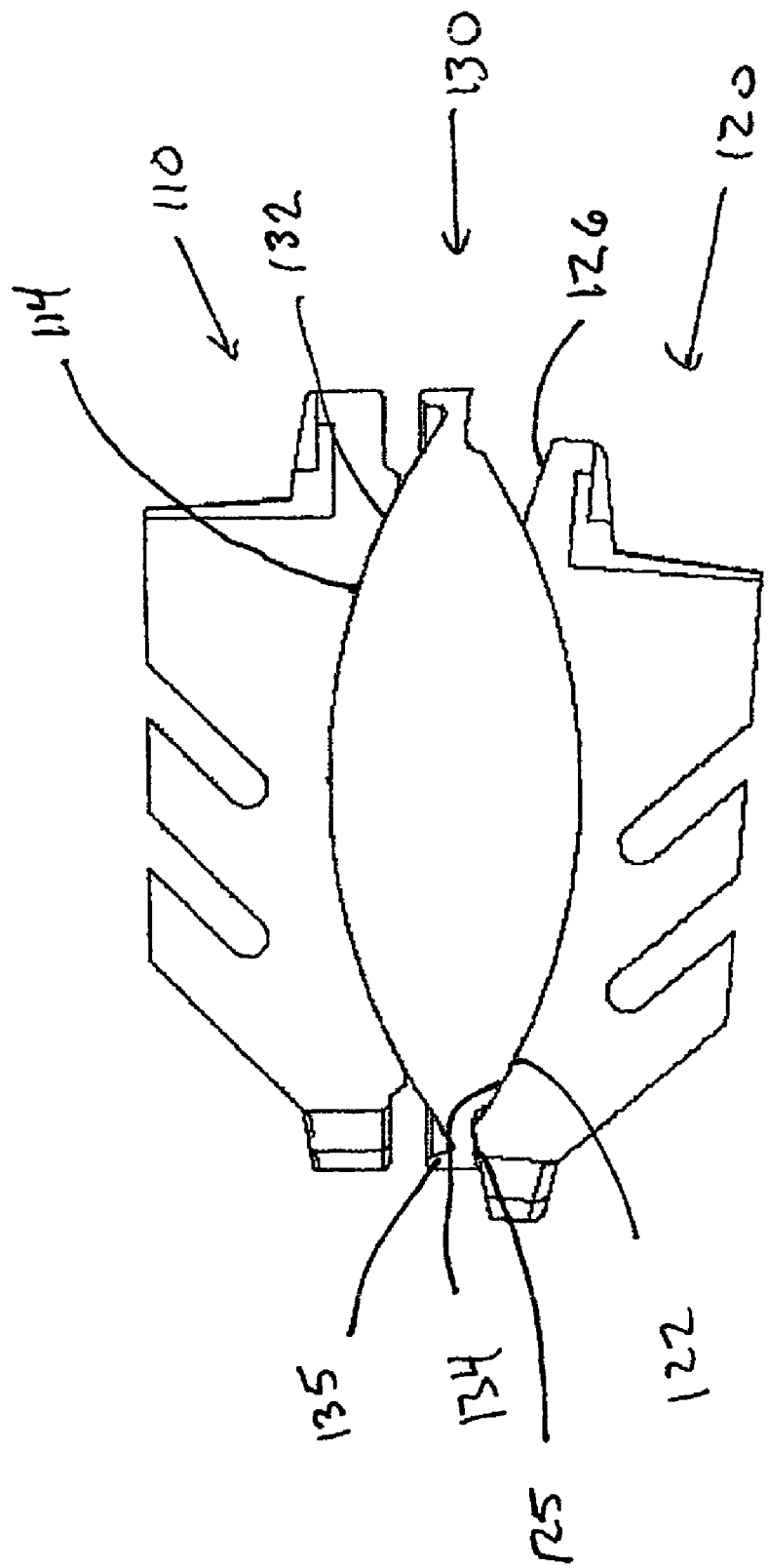
FIG. 18 is an illustration of an embodiment of the prosthetic disc design of the present invention.
Figure 19:
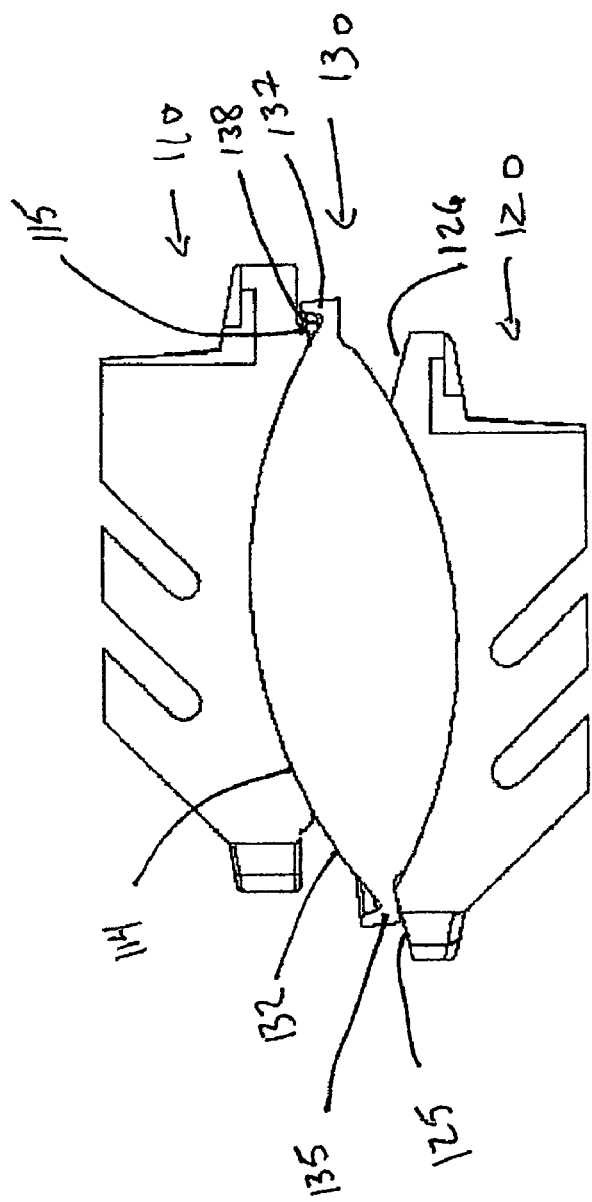
FIG. 19 is an illustration of an embodiment of the prosthetic disc design of the present invention.

FIGS. 18 and 19 simply further illustrate the relative positions of the components of a prosthetic disc during both rotation and translation in the anterior-posterior direction during extension. Similar to the description provided with respect to FIGS. 16 and 17, FIG. 18 illustrates how partially cylindrical surfaces 122 and 134 of the lower endplate 120 and central core member 130, respectively, allow for extension, i.e. rotation in the posterior direction. And similar to the description provided with respect to FIGS. 16 and 17, FIG. 19 illustrates how partially spherical surfaces 114 and 132 of upper endplate 110 and central core member 130, respectively, allow for translation, i.e. substantially linear movement in the axial plane. FIG. 19, in particular, illustrates translation in the anterior direction during extension.

In the embodiments shown in FIGS. 13-19, the third major movement allowed by the prosthetic disc design is rotation in the axial plane. As described previously, lower surface 114 of upper endplate 110 and upper surface 132 of core member 130 are partially spherical. Accordingly, the articulating surfaces allow for axial rotation, in conjunction with the lateral bending and translation provided by the prosthetic disc designs.

The various embodiments of the present invention may have limits on motion or may not. In non-limited motion designs, the prosthetic disc design does not limit the range of movement. Rather, in these designs, the various components of the vertebra, including vertebral bodies, muscles, ligaments, facet joints, and other elements of the body limit the movement of the components of the prosthetic discs. In limited motion designs, mechanical stops are provided to limit the range of movement of the components of the prosthetic disc. The stops may be designed to limit one, two, or more of the various types of movements capable by the prosthetic discs.

For example in one embodiment of the present invention, stops may be provided to limit rotation in the anterior-posterior direction. With reference to FIGS. 16 and 18, core member 130 may be formed with a ring of material designed to interact with endplates 110 and 120 of the prosthetic disc. As seen in FIG. 16, for example, core element 130 is formed with stop 135 that interacts with interacting surfaces 125 and 126 of lower endplate 120 of the prosthetic disc. Accordingly, during flexion as seen in FIG. 16, the interaction between stop 135 and interacting surface 126 of lower endplate 120 limits the amount of rotation that may occur between articulating surface 122 of endplate 120 and surface 134 of core 130. Similarly, FIG. 18 illustrates the interaction between stop 135 and interacting surface 125 of lower endplate 120 during extension.

Figure 20:
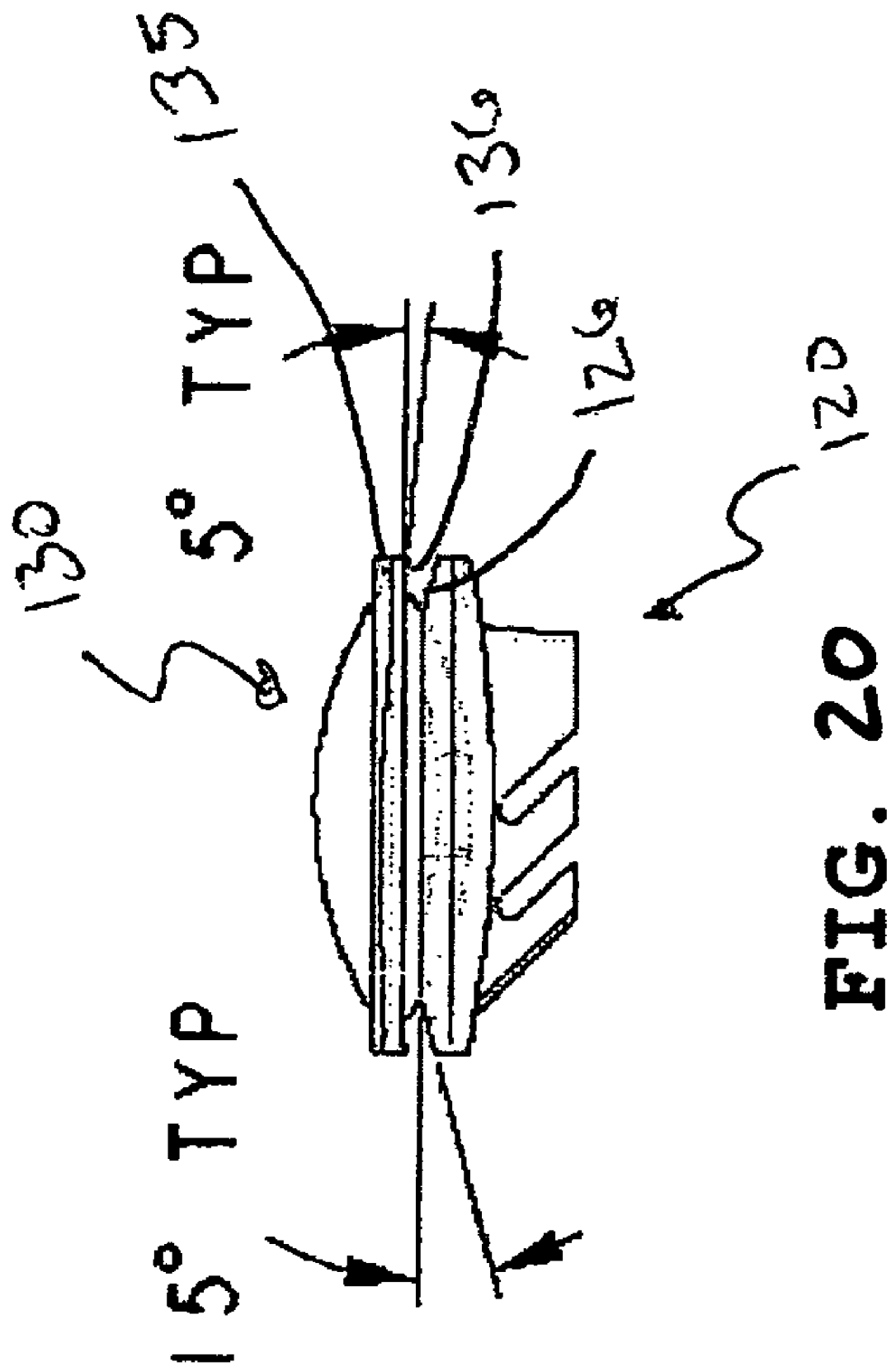
FIG. 20 is an illustration of a core member and bottom endplate in an embodiment of the present invention.
Figure 24A:
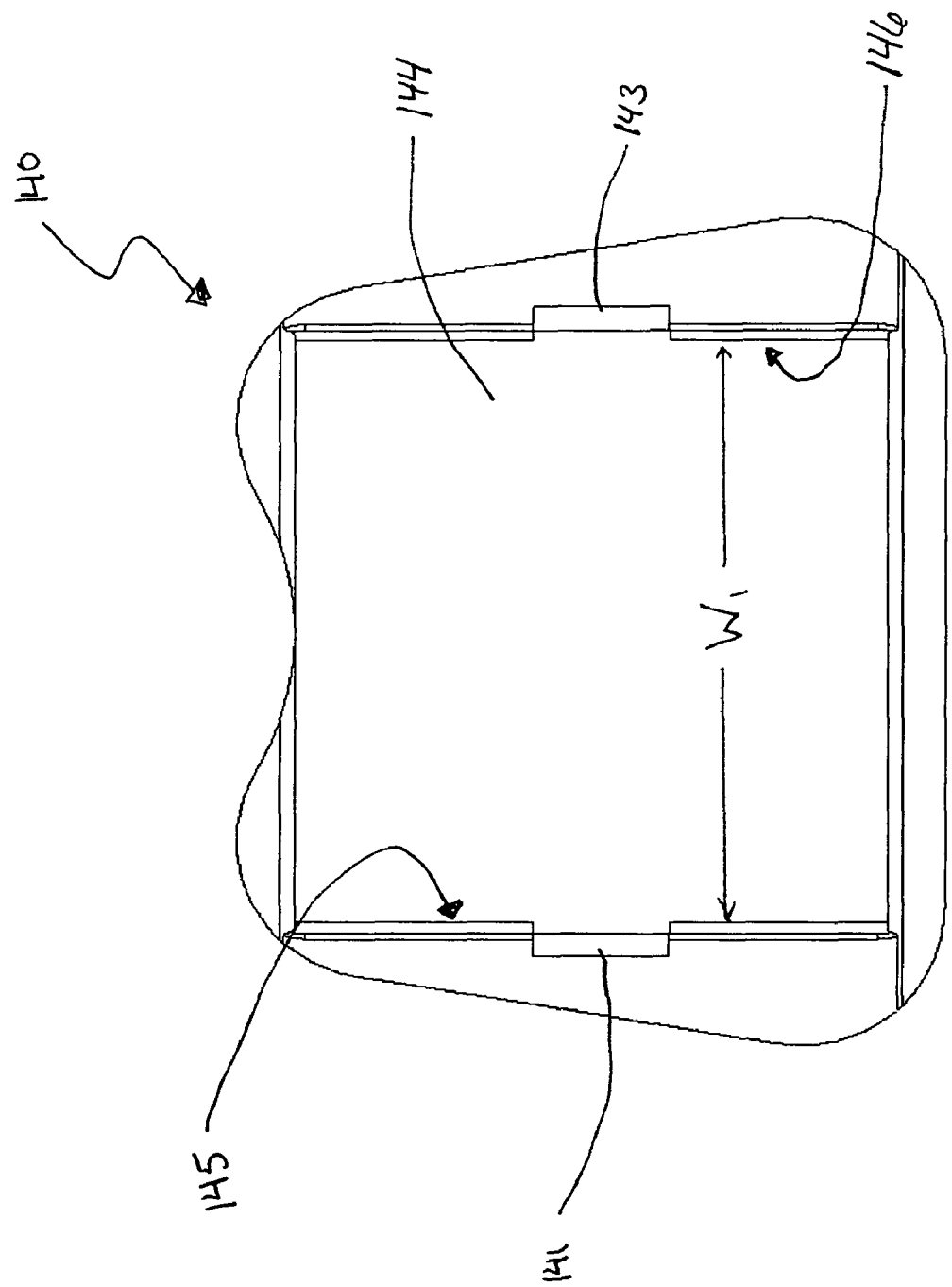
FIG. 24A is an illustration of a core member of an embodiment of the present invention.

Either or both stop 135 or interacting surfaces 125 and 126 of lower endplate 120 may be configured to provide for limits of motion. For example, in one embodiment the stop is configured to limit rotation of the partially cylindrical surfaces of the lower endplate and core member such that rotation may be greater in one direction, i.e. during flexion, than during extension. Alternatively, as described previously, stop and/or interacting surfaces of the lower endplate may be configured with sloped or angled surfaces of varying degrees to precisely control the range of movement. For example and as seen in FIG. 20, stop 135 is configured with an angled surface 136 of 5°. The opposite, interacting surface 126 of endplate 120 is similarly configured with an angled surface of 15°. It would be apparent to one of skill in the art that either one or both of these angled surfaces may be varied to both create a mating surface upon rotation and control the range of motion allowed by the articulating surfaces. And as discussed previously, either or both the stop or interacting surfaces of the lower endplate may have different angles or thickness to provide varying control of motion. Hence, one prosthetic disc design may allow greater degrees of motion during flexion than extension. Alternatively, other disc designs may allow greater degrees of motion during extension than flexion. While any number of variations may be employed within the scope of the present invention, preferably the limitations of flexion and extension approximate the ranges of motion of a normal, healthy disc.

In addition to stops that limit rotation in the lateral plane, the prosthetic discs of the present invention may also provides stops to constrain translational movement. For example, ring 135 about core member 130 may be designed with a lip or rim 137 that rises in the superior direction about the circumference of stop 135 of core member 130. Similarly, upper endplate 110 may be designed with an interacting surface 115 configured to contact the inner portion 138 of lip 137. As seen in both FIGS. 17 and 19, during translation, inner surface 138 of lip 137 contacts interacting surface 115 of upper endplate 110, thus, limiting translation of the components of the prosthetic disc. Again, while the present invention is not limited to any particular ranges of movement, and in fact contemplates unconstrained devices, preferably a stop is provided to limit translation of the prosthetic disc components to approximate the range of motion naturally occurring in a normal, healthy disc.

The stops of the present invention may also be used to prevent the central core member from slipping out of alignment with the upper and lower endplates. Accordingly, lip 137 of core member 130, may prevent core member 130 from coming out of alignment with endplates 110 and 120. Additional stops may be provided that further help prevent the core member from slipping out of alignment. These additional stops may also act as backup stops in the case of a primary stop failure.

Figure 22:
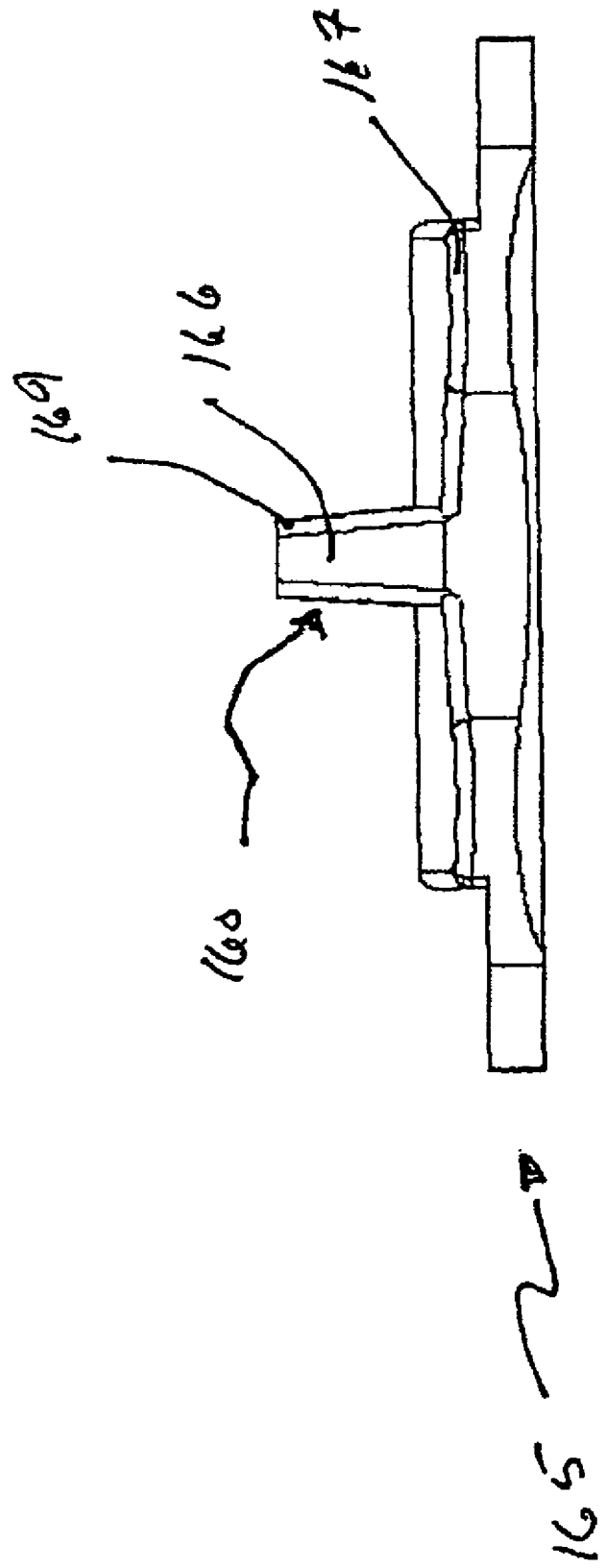
FIG. 22 is an illustration of a core member of an embodiment of the present invention.

For example and with reference to FIGS. 21-24, one embodiment of the present invention contemplates the use of protrusions and cut-outs to act as secondary stops. As seen in FIGS. 21 and 22, central core member 140 may contain protrusions 141 and 143 disposed along lower partially cylindrical surface 144 of core member 140. Protrusions 141 and 143, in this example, are placed along the sides of the cylindrical surface and protrude outward from sidewalls 145 and 146 of lower cylindrical surface 144 of central core member 140. Protrusions 141 and 143 may also be configured with angled surfaces 147 and 148 as seen in FIG. 21. Finally, as seen in FIGS. 21 and 22, protrusions 141 and 143 are placed centrally along the radius of lower partially cylindrical surface 144.

With continuing reference to the above FIGS. 21 and 22 and their corresponding description, lower endplate 150 may further be configured to receive protrusion 141 and 143 of core member 140. As seen in FIGS. 23 and 24, side walls 151 and 152 of upper surface 153 of lower endplate 150 are configured with notches or cut-outs 154 and 155 that receive protrusions 141 and 143 of central core 140. Notches 154 and 155 allow central core element 140 to be placed onto lower endplate 150. Notches 154 and 155 may be designed to allow placement of core element 140 substantially from only one angle, i.e. when core element 140 is lowered onto lower endplate 150 and core element 140 is in a neutral or parallel position relative to endplate 150.

Once inserted, movement of core element 140 relative to endplate 150 is provided by forming grooves 156 and 158 within the sidewalls 151 and 152 of partially cylindrical surface 157 of lower endplate 150. Accordingly, protrusions 141 and 143 ride within grooves 156 and 158, respectively, during flexion and extension. Grooves 156 and 158 are further designed to match or mate with the specific configuration of protrusions 141 and 143. As seen in FIG. 21, protrusions 141 and 143 comprise angled surfaces 147 and 148. Accordingly, as seen in FIG. 23, grooves 156 and 158 are configured to mate with angled surfaces 147 and 148 of protrusions 141 and 143. In this particular embodiment, as core element 140 moves relative to lower endplate 150 along their respective articulating surfaces, protrusions 141 and 143 travel within grooves 156 and 158 respectively along the partially cylindrical lower surface 157 of the lower endplate 150.

Grooves 156 and 158 may act as stops to limit flexion and extension. In this embodiment of the present invention, grooves 156 and 158 are designed with endpoints (two endpoints within each groove) to interact with protrusions 141 and 143. Accordingly, in one embodiment, grooves 156 and 158 do not run the entire length of partially cylindrical lower surface 157. While any number of variations may be provided, in one embodiment, the length of grooves 156 and 158 allow for a range of movement that substantially matches the range of movement allowed for by stop 135 and interacting surfaces 125 and 126 of FIG. 18. In this manner, the prosthetic disc contains two mechanisms by which rotation is limited, while each mechanism constrains the device in the same degree. Alternatively, grooves 156 and 158 may be designed such that movement of core element 140 is limited less than what is allowed by stops 135 and interacting surfaces 125 and 126 of FIG. 18. In this manner, the limiting mechanism of grooves 156 and 158 and protrusions 141 and 143 act as secondary or back-up stops in case of primary stop failure.

Another aspect of protrusions 141 and 143 and grooves 156 and 158 contemplated by the present invention is their use in limiting separation of core element 140 from lower endplate 150. For example, angled surfaces 147 and 148 of protrusions 141 and 143 may interact with the matching surfaces of grooves 156 and 158. Accordingly, any force acting to separate core element 140 from lower endplate 150, is resisted by the interaction between protrusions 141 and 143 and their corresponding grooves 156 and 158. In this manner, core element 140 can be secured from separation from lower endplate 150.

In an alternate embodiment, the second endplate may be configured with cut-outs rather than grooves. In this embodiment of the present invention, the cut-outs are configured to receive the tabs or protrusions of the core element. Rather than riding within grooves as discussed above, the protrusions are sized smaller than the cut-outs. Accordingly, during articulation between the surfaces of the core element and the second endplate, the protrusions move within the spaces created by the cut-outs. Depending on the size of the cut-outs, the protrusions may abut or come into contact with the sidewalls of the cut-outs, thus limiting movement of the core element relative to the second endplate. By varying the size of the cut-outs and protrusions, varying degrees of articulation may be achieved in different prosthetic disc designs. As with the discussion relating to the protrusions and grooves described above, the protrusions and cut-outs may serve as primary or secondary stops.

In an alternate embodiment and with reference to FIGS. 21 to 24A, the partially cylindrical surface 157 of second endplate 150 may be bound by sidewalls 149 and 159 that are arcuate in shape. Additionally, the width $W_1$ of the partially cylindrical surface 144 of core 140 may be slightly smaller than width $W_2$ of the partially cylindrical surface 157 of second endplate 150. Also, as seen in this embodiment, the sidewalls 145 and 146 of the core member may be linear or straight. In this embodiment, in addition to the anterior-posterior rotation provided by the partially cylindrical surfaces of the core member 140 and second endplate 150, this configuration also allows rotation of the core member 140 relative to the second endplate 150 in the coronal plane. As one of skill in the art would understand, rotation of the core member 140 relative to second endplate 150 is limited by the interaction of sidewalls 145 and 146 of the core member and sidewalls 149 and 159 of the second endplate. Additionally, $W_1$ and $W_2$ may be varied to control the range or amount of rotation in the coronal plane.

As discussed previously, the endplates of the prosthetic disc may also be configured to engage more securely with the vertebral bodies that they contact. For instance, one or more raised ridges or keels may extend at least partially into the endplate of the vertebral body. The vertebral body likewise may be prepared by cutting a similar number of grooves or channels that will receive the keels. The grooves or channels may help guide the assembly into proper position in the treated area. This feature may be particularly beneficial when a certain orientation of the assembly relative to the vertebral body is desired.

In one embodiment of the present invention, the upper and lower portions of a disc assembly may be configured with a keel that can engage with or contact a neighboring vertebral body. One advantage of providing a keel is that it may be used to guide the assembly into position during insertion into a treated area of the spine. A channel or groove may be cut out of a vertebral body next. Then, a physician may insert the assembly into the vertebral body so that the keel slides in the groove or channel. The keel and grove may be substantially linear or straight, or alternatively, may be curved or arched so that the assembly rotates and slides into position. The ridges or keels and corresponding channels or grooves also may be straight or curved to match the desired insertion path of the assembly. The grooves or channels formed in a vertebral body may help achieve the proper orientation and distance of the assemblies and provide for a secure anchoring of the endplate.

The cross-sectional profile of the keel may have different shapes. For instance, the cross-sectional profile of the keel may have the shape of a wedge, a truncated wedge, a rectangle, or a square. The channel or groove may be cut to have a cross-sectional profile corresponding approximately to the shape of the keel. One advantage of the keel having a truncated wedge cross-section is that a similarly shaped channel or groove may ensure that the keel engages with the bony surface. This configuration may also provide increased resistance to expulsion of the disc assembly.

Figure 25:
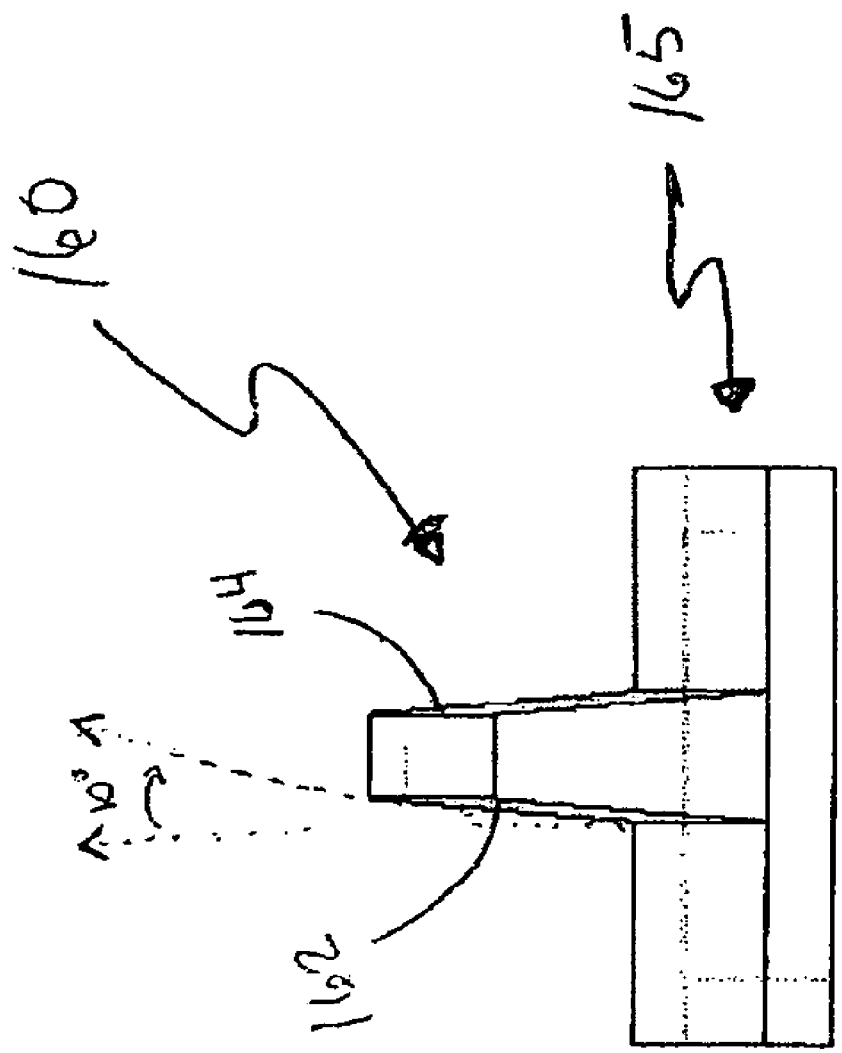
FIG. 25 is an illustration of an endplate of an embodiment of the present invention.

In one embodiment, the cross-section of a ridge or keel may be triangular or have a truncated triangular shape. For example, as shown in FIG. 25, keel 160 is of a truncated triangular shape. The height of keel 160 may vary, but may be configured with sloped sides 162 and 164, as shown in FIG. 25, of about 10° from the longindutinal plane. The height of keel 160 may vary, but in general is designed to provide sufficient contact area once inserted in the vertebral body to anchor endplate 165. The keel may be sized such that any groove or channel cut into the vertebral body to accommodate the keel does not substantially impact the structural integrity of the vertebral body.

The use of one or more keels may also increase bone to implant surface contact, thereby decreasing the likelihood that the assembly will shift or move about of position. In one embodiment, the increase in surface contact may be about 5% or more, which in another embodiment the increase may be about 15% or more.

Over time, it is believe that the stability of the disc assembly in the treated area will further increase as bone growth engages with outer surfaces of the disc assembly. To facilitate this growth and increased stability, all or part of the surfaces of the disc assembly that engages or otherwise contacts bone may be treated to promote bony on-growth. For instance, titanium plasma may be provided on the keel or other portions of the assembly to provide a matrix for bone growth. In addition, the keel may be configured with notches, slots, or openings formed along its length. As bone grows into these openings, the disc assembly will become more securely anchored in place.

Figure 26:
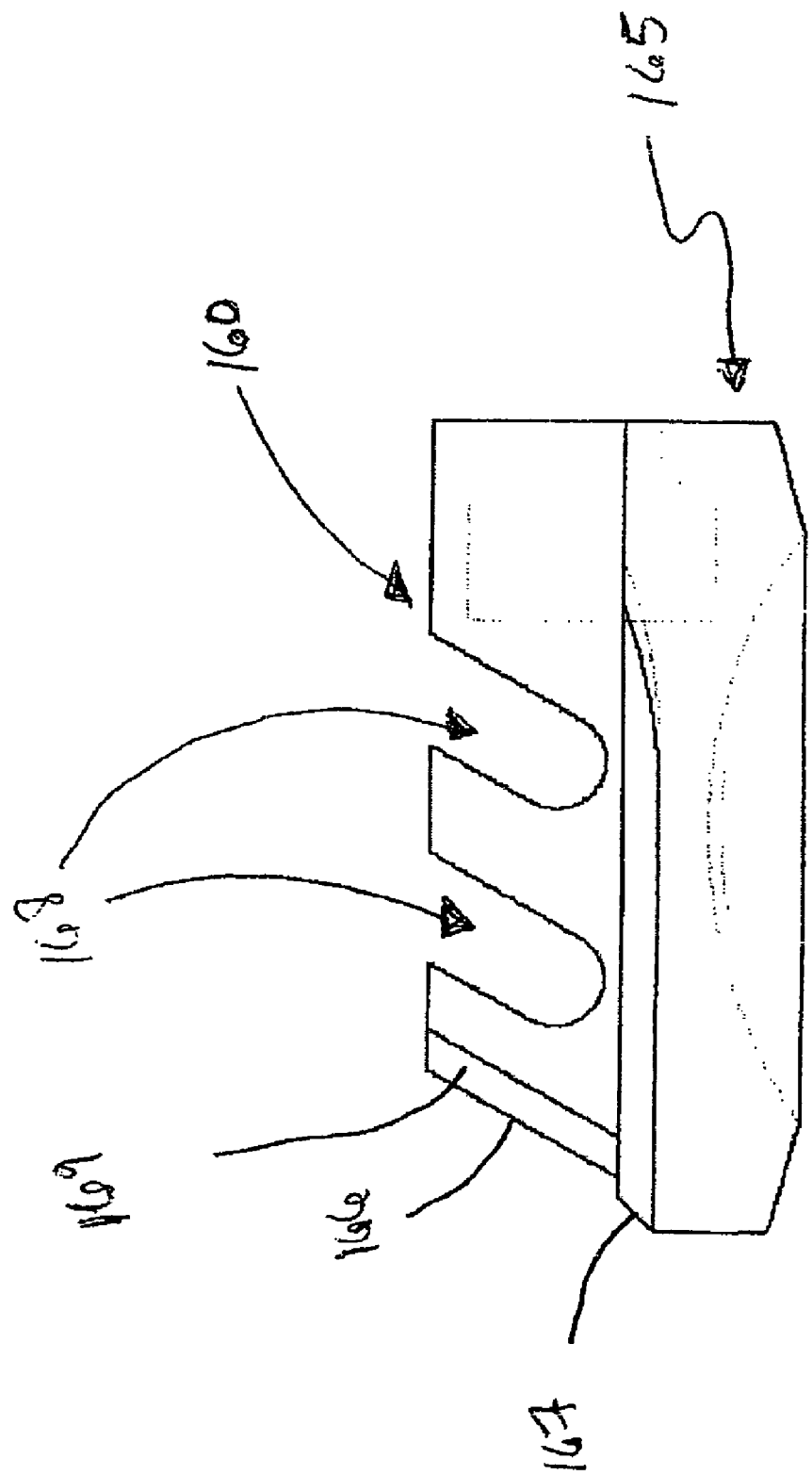
FIG. 26 is an illustration of an endplate of an embodiment of the present invention.

As a disc assembly is first inserted into a treated area, it may need to be repositioned, rotated or otherwise moved. For instance, repositioning the disc assembly may be needed so that the keel can properly engage with the channel or groove. As shown in FIGS. 26 and 27, keel 160 of endplate 165 has an angled first leading edge 166. Additionally, endplate 165 may be configured with a second leading edge 167 that does not contain part of keel 160. Thus, in one embodiment the assembly can be partially inserted into the treated area without keel 160 engaging with or contacting the vertebral body. In one embodiment, the length of second leading edge 167 is from about 1 mm to about 10 mm, while in another embodiment second leading edge 167 is from about 2 mm to about 5 mm. Alternatively, the length of second leading edge 167 may be from about 1% to about 20% of the length of the endplate 165 on which it is disposed, or may be from about 2% to about 10%. The length of the endplate 165 may be determined by measuring the longitudinal central axis of the portion or endplate on which second leading edge 167 is disposed.

In addition, referring again to FIG. 26, keel 160 may have first leading edge 166 that is sloped or gradually increases in height. As seen in FIGS. 26 and 27, first leading edge 166 is sloped. Providing a ramped first leading edge 166 may aid in aligning and inserting keel 160 into a groove or channel formed in a vertebral body.

As mentioned previously, the keel of a disc assembly may be configured to promote or permit bony ongrowth/ingrowth that may help hold the disc assembly in place more securely. FIG. 26 further illustrates an embodiment of keel 160 having a plurality of slots or cuts 168 formed in it. In FIG. 26, slots 168 may extend at an angle, such as from about 5° to about 40° off from a vertical direction, and more preferably from about 10° to about 30°. Keel 160 may have two or more, or even three or more slots or cuts. One skilled in the art would appreciate that other configurations may also be used to promote bony ongrowth/ingrowth that might help further secure the disc assembly in place. For instance, the keel may have holes or apertures drilled into it, longitudinal or horizontal slots may be formed, and the sidewalls of the keel may be textured with one or more grooves or channels that does not extend fully through the keel to the opposing sidewall.

In addition, the face of the keel that is first inserted into a groove or channel may have a taper or chamfer. One potential advantage of configuring a keel with a taper or chamfer on its face is that it may assist in aligning the keel with the opening of the channel or groove. In addition, a chamfered or tapered face may help reduce drag forces and undesired cutting or gouging of the channel or groove as the keel is pushed toward its final position. As seen in FIG. 26, the face of keel 160 is configured with a chamfer 169 to aid in the insertion of the prosthetic disc.

In alternative embodiments, the endplate or keel may be formed with one or more interiorly threaded holes located on the anterior edge of the endplate or keel. These interiorly threaded holes may be configured for attachment with a tool. For example, the interiorly threaded holes may be configured to engage with a tool having exteriorly threaded protrusions. In this example, the protrusions of the tool would mate with the holes of the endplates and hence, the tool may engage, hold, or otherwise capture the endplates of the prosthetic disc assembly. The tool may be designed to hold a single endplate or alternatively may be designed to hold both endplates and the core member as a unit and in a rigid state. The tool may then be used to implant the prosthetic disc into the intervertebral space.

As discussed previously, prosthetic disc designs of the present invention may be comprised of a plurality of assemblies. For example, prosthetic disc designs may be comprised of two assemblies. In a two assembly design, each assembly may be comprised of an upper endplate, a central core member, and a lower endplate. One advantage to the two assembly design is that it may be made of a smaller dimension and hence provide for ease of implantation, which may be especially useful in minimally invasive implantation techniques. Another advantage of two assembly designs is that they may be used where the vertebral bodies to which the prosthetic discs will be in contact with are diseased or otherwise not susceptible to supporting a prosthetic disc with a central keel. A two assembly design subjects the outer sides of the vertebral body to contact. Another advantage to a two assembly design is that it may allow for increased contact surface area while minimizing the size of the prosthetic disc. Accordingly, if a surgeon wishes to minimize distraction of organs and other body parts during an anterior approach to the vertebra, they may select a two assembly design which may not require as large of a surgical pathway. In this case, the surgeon may implant a first assembly through the surgical pathway and then implant a second assembly through the surgical pathway. Accordingly, a surgeon may be able to minimize the size of a surgical pathway to a size just large enough to implant one assembly, yet maintain the advantage of implanting a prosthetic disc that has a large contact surface area.

A plurality of disc assemblies having varying heights, widths, lengths, and ranges of translation and rotation capability may be provided in a kit to a physician so that the final selection of the proper disc assembly can be made during the surgical procedure. For instance, a plurality of disc assemblies may be provided having disc heights varying from about 5 mm to about 25 mm. In one embodiment, the disc heights may differ by a uniform increment, such as differing by about 1 mm or by about 1.5 mm within a range.

Likewise, the length of the disc assembly may be varied to accommodate different anatomies. For instance, disc assemblies may have longitudinal axes that range from about 8 mm to about 35 mm. Incremental changes in the length of the assemblies may also be provided in a kit, such as by providing disc assemblies of different lengths in 2 mm increments. In another embodiment, a plurality of assemblies may have at least 2 different lengths that differ by more than about 3 mm. For instance, one set of disc assemblies may have a length of about 25 mm, while another set is about 28 mm in length. The length of the disc assembly preferably may be selected to maximize implant/endplate contact area.

A plurality of assemblies may also be provided with differing ranges of axial rotation. For instance, one or more assemblies may have no restriction on rotational movement, or may have stops or other devices that prevent rotation only after the rotation has exceeded the range of motion of a natural, healthy spine.

Other disc assemblies of the present invention may permit a range of axial rotation in one direction, but restrict it in the opposite direction. In other words, a disc assembly of this embodiment may permit limited disc rotation so that a patient may rotate or turn their body to one side or in one direction, but not in the other. For example, a disc assembly may allow rotation or movement between a 0° position, where the spine is not rotated or turned, to up to about 5°, up to about 8°, up to about 10°, or up to about 15° in one direction only.

Various instruments and tools may be used to implant anterior prosthetic discs disclosed. For example, in one embodiment, the prosthetic discs are implanted using a distractor. In this embodiment, the adjacent vertebra are distracted and the damaged disc is removed. While distracted, the distractor is placed into the intervertebral space. The distractor is designed to maintain spacing between the adjacent vertebra and provided a space to insert the prosthetic disc. In one embodiment, the distractor may have interior protrusions spaced to accept and support the individual components of the prosthetic disc. Following insertion of the distractor, each individual component may be inserted into the distractor and held in position. The distractor may then be removed and the force of the contracting vertebral bodies compacts the components of the prosthetic disc into place.

Alternatively, a tool holder may be provided that is capable of holding the assembled components of the prosthetic disc. Accordingly, with or without the distractor in place, the surgeon may insert all components of the prosthetic disc with the tool holder into the intervertebral space.

As described above, a cylindrical surface may be provided in a disc assembly in addition to a second, curved surface corresponding to a portion of a sphere. One feature of this combination of surfaces is that the disc can permit translation between the upper vertebral body and the lower vertebral body.

In one embodiment, the disc is capable of permitting translation of up to about 1 mm in the anterior-posterior direction, while in another embodiment the disc is capable of translation of up to about 5 mm. Some disc assemblies may permit even more translation, such as up to about 7 mm or even up to about 10 mm. As described above, mechanical stops may be provided to limit the range of motion of the disc assembly.

The various features and embodiments of the invention described herein may be used interchangeably with other features and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

What is claimed is:

1. An intervertebral prosthetic disc comprising:
   a first endplate having a first surface configured to substantially engage with a first vertebral body and a second surface comprising a contoured, partially spherical articulating surface;
   a second endplate having a first surface configured to substantially engage with a second vertebral body and a second surface comprising a contoured, partially cylindrical articulating surface, the second endplate including a sidewall including one or more notches formed therein;
   a core element at least partially disposed between the first and second endplates,
   wherein the core element comprises a first contoured surface in communication with and substantially corresponding to the curvature of the second surface of the first endplate, and a second contoured surface substantially in communication with and substantially corresponding to the curvature of the second surface of the second endplate, wherein the first surface of the first endplate has a first keel configured to engage with a groove in the first vertebral body and the first surface of the second endplate has a second keel configured to engage with a groove in the second vertebral body, wherein at least one of the first and second keels has at least one slot extending a length downwardly from a distal edge of the keel to the base of the keel, and wherein the at least one of the first and second keels includes a leading edge that includes a chamfer for aligning and inserting the keel into the groove in the first and second vertebral body.

2. The intervertebral prosthetic disc of claim 1, wherein the partially cylindrical articulating surface of the second endplate permits rotation of the second endplate relative to the core element substantially in the sagittal plane.

3. The intervertebral prosthetic disc of claim 1, wherein the partially spherical articulating surface of the second surface of the first endplate permits rotation of the first endplate relative to the core element substantially in all planes.

4. The intervertebral prosthetic disc of claim 1, wherein the core element comprises a stop formed by a ring of material about the circumference of the core element.

5. The intervertebral prosthetic disc of claim 1, wherein the stop of the core element interacts with a upper surface of the second endplate to limit rotation of the second endplate relative to the core element.

6. The intervertebral prosthetic disc of claim 5, wherein the stop of the core element interacts with a lower surface of the first endplate to limit translation of the first endplate relative to the core element.

7. The intervertebral prosthetic disc of claim 1, wherein at least a portion of the at least one slot near the base of the keel is substantially arcuate.

8. An intervertebral prosthetic disc comprising:
a first endplate having a first surface configured to substantially engage with a first vertebral body and a second surface comprising a contoured, partially spherical articulating surface;
a second endplate having a first surface configured to substantially engage with a second vertebral body and a second surface comprising a contoured, partially cylindrical articulating surface, the second endplate including a sidewall including one or more notches formed therein;
a core element at least partially disposed between the first and second endplates,
wherein the core element comprises a first contoured surface in communication with and substantially corresponding to the curvature of the second surface of the first endplate, and a second contoured surface substantially in communication with and substantially corresponding to the curvature of the second surface of the second endplate;
wherein the second surface of the core element comprises a first width, wherein the second surface of the second endplate comprises a second width, the first width and second widths configured to permit rotation of the core element relative to the second endplate in the coronal plane
wherein the first surface of the first endplate has a first keel configured to engage with the first vertebral body and the first surface of the second endplate has a second keel configured to engage with the second vertebral body,
wherein at least one of the first and second keels has at least one slot extending a length downwardly from a distal edge of the keel to the base of the keel, substantially adjacent to one of the first and second surface of one of the first and second endplate, and
wherein the at least one slot extends substantially obliquely from the distal edge of the keel to the base of the keel at an angle of about 10° to about 30° from a vertical axis.

9. The intervertebral prosthetic disc of claim 8, wherein at least a portion of the at least one slot near the base of the keel is substantially arcuate.

\* \* \* \* \*